United States Patent
Dartmann et al.

(10) Patent No.: US 10,577,661 B2
(45) Date of Patent: Mar. 3, 2020

(54) METHOD FOR BREAST CANCER RECURRENCE PREDICTION UNDER ENDOCRINE TREATMENT

(71) Applicant: Myriad International GmbH, Cologne (DE)

(72) Inventors: Mareike Dartmann, Cologne (DE); Inke Sabine Feder, Cologne (DE); Mathias Gehrmann, Cologne (DE); Guido Hennig, Eschburn (DE); Karsten Weber, Cologne (DE); Christian Von Törne, Cologne (DE); Ralf Kronenwett, Cologne (DE); Christoph Petry, Cologne (DE)

(73) Assignee: MYRIAD INTERNATIONAL GMBH, Cologne (DE)

( * ) Notice: Subject to any disclaimer, the term of this patent is extended or adjusted under 35 U.S.C. 154(b) by 427 days.

(21) Appl. No.: 15/234,828

(22) Filed: Aug. 11, 2016

(65) Prior Publication Data

US 2017/0067118 A1   Mar. 9, 2017

Related U.S. Application Data

(63) Continuation of application No. 13/638,360, filed as application No. PCT/EP2011/054855 on Mar. 29, 2011, now abandoned.

(30) Foreign Application Priority Data

Mar. 31, 2010  (EP) .................................... 10158561

(51) Int. Cl.
    *C12Q 1/6886*  (2018.01)
(52) U.S. Cl.
    CPC ...... *C12Q 1/6886* (2013.01); *C12Q 2600/118* (2013.01); *C12Q 2600/158* (2013.01)
(58) Field of Classification Search
    None
    See application file for complete search history.

(56) References Cited

U.S. PATENT DOCUMENTS

| | | | |
|---|---|---|---|
| 2006/0024692 A1 | 2/2006 | Nakamura et al. | |
| 2006/0166231 A1 | 7/2006 | Baker et al. | |
| 2006/0234287 A1 | 10/2006 | Erlander et al. | |
| 2007/0099209 A1* | 5/2007 | Clarke et al. | C12Q 1/6886 435/6.12 |
| 2007/0134688 A1 | 6/2007 | Symmans et al. | |
| 2008/0125581 A1 | 5/2008 | Deming et al. | |
| 2010/0105564 A1 | 4/2010 | Park et al. | |
| 2011/0145176 A1 | 6/2011 | Perou et al. | |
| 2011/0306513 A1 | 12/2011 | Song et al. | |
| 2012/0065084 A1 | 3/2012 | Sotiriou et al. | |
| 2012/0142624 A1 | 6/2012 | Yang et al. | |
| 2014/0349878 A1 | 11/2014 | Wang et al. | |

FOREIGN PATENT DOCUMENTS

| | | | |
|---|---|---|---|
| EP | 1134738 | 9/2001 | |
| EP | 2036988 | 3/2009 | |
| EP | 2163649 | 3/2010 | |
| EP | 2553118 | 2/2013 | |
| WO | 2003001985 | 1/2003 | |
| WO | 2006084272 | 8/2006 | |
| WO | 2006119593 | 11/2006 | |
| WO | WO-2006119593 A1 * | 11/2006 | .......... C12Q 1/6886 |
| WO | 2006138275 | 12/2006 | |
| WO | 2006133923 | 3/2007 | |
| WO | 2008006517 | 1/2008 | |
| WO | 2008070571 | 6/2008 | |
| WO | 2008079269 | 7/2008 | |
| WO | 2008154249 | 12/2008 | |
| WO | 2009095319 | 8/2009 | |
| WO | 2009114836 | 9/2009 | |
| WO | 2009132928 | 11/2009 | |
| WO | 2009158143 | 12/2009 | |
| WO | 2010003771 | 1/2010 | |
| WO | 2010003773 | 1/2010 | |
| WO | 2010076322 | 7/2010 | |
| WO | 2011120984 | 10/2011 | |
| WO | 2011121028 | 10/2011 | |
| WO | 2012153187 | 11/2012 | |
| WO | 2013014296 | 1/2013 | |
| WO | 2015121300 | 8/2015 | |

OTHER PUBLICATIONS

Affymetrix Genechip bHuman Genome U133 plus 2.0 Array, GEO.
Chanrion et al., "A gene expression signatures that can predict the recurrence of tamoxifen-treated primary breast cancer", Clinical Cancer Research, 2008, pp. 1744-1752.
Dondoni et al., Angew Cehm Int Ed Engl, 2008, vol. 47, No. 47, pp. 8995-8997.
European Communication from Application No. 12740974.6, dated May 11, 2015.

(Continued)

*Primary Examiner* — Kaijiang Zhang
(74) *Attorney, Agent, or Firm* — FisherBroyles LLP; Victoria L. Boyd; Jason M. Pass

(57) ABSTRACT

The present invention relates to methods, kits and systems for the prognosis of the disease outcome of breast cancer, said method comprising:
(a) determining in a tumor sample from said patient the RNA expression levels of at least 2 of the following 9 genes: UBE2C, BIRC5, RACGAP1, DHCR7, STC2, AZGP1, RBBP8, IL6ST, and MGP
(b) mathematically combining expression level values for the genes of the said set which values were determined in the tumor sample to yield a combined score, wherein said combined score is indicative of a prognosis of said patient; and kits and systems for performing said method.

19 Claims, 3 Drawing Sheets
Specification includes a Sequence Listing.

(56) References Cited

OTHER PUBLICATIONS

European Communication Response from Application No. 11710526.2, dated Aug. 19, 2015.
European Communication Response from Application No. 11710526.2, dated Dec. 22, 2014.
European Communication Response from Application No. 12740947.6, dated Jul. 2, 2014.
European Communication Response from Application No. 12740947.6, dated Sep. 10, 2015.
European Communication Response from Application No. 16184484.0, dated Nov. 15, 2016.
European Intention to Grant from Application 12740974.6 dated Jun. 15, 2016.
European Intention to Grant from Application 14188791.9, dated Oct. 29, 2015.
European Intention to Grant from Application No. 12740974.6, dated Nov. 19, 2015.
Extended European Search Report from Application 14188791 dated Feb. 6, 2015.
Extended European Search Report from Application 16184484.0 dated Feb. 9, 2017.
Extended European Search Report from Application No. 16159481.7, dated Sep. 8, 2016.
Extended European Search Report from Application No. 16184484.0, dated Feb. 9, 2017.
Henderson et al., Journal of Clinical Oncology, vol. 21, No. 6, 2003, pp. 976-983.
Hess et al., Journal of Clinical Oncology, vol. 29, No. 34, 2011, pp. 4516-4525.
Hou et al., J Neurosci Meth, Oct. 2005, vol. 148, No. 1, pp. 60-70.
International Preliminary Report from Application PCT/EP2012/064865, dated Jan. 28, 2014.
International Search Report from Application No. PCT/EP11/054855, dated Sep. 21, 2011.
International Search Report from Application No. PCT/EP2012/064865, dated Jan. 31, 2013.
International Search Report from Application No. PCT/US10/024603, dated Sep. 28, 2010.
International Written Opinion from Application No. PCT/EP2012/064865 dated Dec. 17, 2012.
Jemal et al., CA Cancer J Clin, 2011, vol. 61, No. 2, pp. 134.
Liedtke et al., Journal of Clinical Oncology, 2009, vol. 27, No. 19, pp. 3185-3191.
Lin et al., J Neurochem, Jan. 2008, vol. 104, No. 2, pp. 400-408.
Loussouarn et al., "Validation of UBE2C protein as a prognostic marker in node-positive breast cancer", British Journal of Cancer, 2009, vol. 101, No. 1, pp. 166-173.
Misset et al., Journal of Clinical Oncology, 1996, vol. 14, No. 4, pp. 1136-1145.
Nowak et al., Nature, May 2002, vol. 417, No. 6887, pp. 424-428.
Paik et al., "A multigene assay to predict recurrence of tamoxifen-treated node-negative breast cancer" New England Journal of Medicine, 2004, vol. 351, No. 27, pp. 2817-2826.
Partial European Search Report from Application No. 11175852, dated Nov. 9, 2011.
Rosemary A. L. Bayne, Molecular Profiling of the Human Testis Reveals Stringent Pathway-Specific Regulation of RNA Expression Following Gonadotropin Suppression and Progestogen Treatment, Journal of Andrology, 2008, vol. 29, No. 4, pp. 389-403.
Russian First Office Action from Application 2012146343/10(074392).
Russian Second Office Action from Application 2012146343/10(074392).
Russian Third Office Action from Application 2012146343/10(074392).
Russian Forth Office Action from Application 2012146343/10(074392).
Soonmyung et al., "Technology Insight: application of molecular techniques to formalin-fixed parrafin-embedded tissues from breast cancer", Natures Clinical Practice Oncology, vol. 2, No. 5, 2005, pp. 246-254.
Sorlie et al., "Gene expression patterns 1-15 of breast carcinomas distinguish tumor subclasses with clinical implications", Proceedings of the National Academy of Sciences of the United States, 2001, vol. 98, No. 19, pp. 10869-10874.
Sotiriou et al., Journal of the National Cancer Institute, 2006, vol. 98, No. 4, pp. 262-272.
Tabchy et al., Clinical Cancer Research, 2010, vol. 16, No. 21, pp. 5351-5361.
Takahashi H., et al., Cancer diagnosis marker extraction for soft tissue sarcomas based on gene expression profiling data by using projective adaptive resonance theory (PART) filtering method, BMC Bioinformatics, 2006, 7, 399, pp. 1-11.
Taylor et al., Breast Cancer Research, vol. 12, No. 3, pp. R39.
Terasaka S., et al., Using a Customized DNA Microarray for Expression Profiling of the Estrogen-Responsive Genes to Evaluate Estrogen Activity among Natural Estrogens and Industrial Chemicals, Environmental Health Perspectives, 2004, vol. 112, No. 7, pp. 773-781.
Tian et al., Tissue Eng Mar.-Apr. 2005, vol. 11, No. 3-4, pp. 513-525.
Von Minckwitz et al., Cancer Research, vol. 69, No. 24, Suppl. 1, 2009, pp. 635S.
Wray et al., vol. 121, No. 21, Apr. 8, 2013, pp. 4359-4365.
Canadian Office Action Response from Application No. 2,793,133 dated Aug. 21, 2018, 2 pages.
European Intention to Grant from Application 16184484.0, dated Jun. 22, 2018, 7 pages.
O'Neill et al., Molecular Cancer, 2013, vol. 12, No. 69, pp. 1-9.
Pockaj et al., Annals of Surgical Oncology, vol. 11, No. 3, 2004, pp. 328-339.
Rathnagiriswaran et al., Mar. 2010, Int. J. Oncol. vol. 36, No. 3, p. 607-616.
Ross et al., The Oncologist, vol. 13, No. 5, 2008, pp. 477-493.
Russian Fifth Office Action from Application 2012146343/10(074392).
Russian Office Action Response from Application No. 2012146343, dated Nov. 7, 2016.
Saito-Hisaminato et al., DNA Research, vol. 9, 2002, pp. 35-45.
Shapiro et al., N Engl J Med, vol. 344, 2001, pp. 1997-2008.
Vandesompele et al., Genome Biology, vol. 3, 2002, pp. 1-11.
Veer et al., Nature, vol. 415, 2002, pp. 530-536.
Vegran et al., British Journal of Cancer, 2009, vol. 101, No. 8, pp. 1357-1364.
Villeneuve et al., Breast Cancer and Treatment, vol. 96, No. 1, 2006, pp. 17-39.
Wang et al., Cancer Letters, vol. 272, No. 2, 2008, pp. 277-284.
Wang et al., Lancet, vol. 365, No. 9460, 2005, pp. 671-679.
Zhijuan et al., Oncology Reports, vol. 20, 2008, pp. 325-332.
Akech et al., Biochemical and Biophysical Research Communications, vol. 333, No. 1, 2005, pp. 35-41.
Andre et al., JCO, vol. 26, No. 16, 2008, pp. 2636-2643.
Benner et al., Trends in Genetics, vol. 17, 2001, pp. 414-418.
Canadian Office Action from Application No. 2,793,133 dated Feb. 7, 2017.
Canadian Office Action Response from Application No. 2,793,133 dated Jul. 18, 2017.
Cheung et al., Nature Genetics, vol. 33, 2003, pp. 422-425.
Couzin-Frankel et al., Science, vol. 329, 2010, pp. 614-615.
Dai et al., Cancer Research, vol. 65, No. 10, 2005, pp. 4059-4066.
Decock et al., BMC Cancer, vol. 8, No. 1, 2008, pp. 1-8.
Desmedt et al., Cell Cycle, vol. 5, No. 9, 2006, pp. 2198-2202.
Dorssers et al., Breast Cancer Research, vol. 7, No. 1, 2004, pp. R82-R92.
Esteva et al., Clin. Cancer Res, vol. 11, 2005, pp. 3315-3319.
European Communication from Application No. 11710526.2, dated Aug. 22, 2013.
European Communication from Application No. 14705056.1, dated Aug. 24, 2016.

(56) References Cited

OTHER PUBLICATIONS

European Communication from Application No. 15702464.7, dated Aug. 30, 2017.
European Communication from Application No. 16184484.0 dated Oct. 18, 2017.
European Communication Response from Application No. 11710526.2, dated May 2, 2013.
European Communication Response from Application No. 11710526.2, dated Feb. 17, 2014.
European Communication Response from Application No. 12740974.6, dated Mar. 11, 2016.
European Communication Response from Application No. 14188791.9, dated Aug. 19, 2015.
European Communication Response from Application No. 14188791.9, dated Dec. 22, 2014.
European Communication Response from Application No. 14705056.1, dated Nov. 22, 2016.
European Communication Response from Application No. 15702464.7, dated Mar. 2, 2017.
European Communication Response from Application No. 16184484.0, dated Sep. 20, 2017.
European Intention to Grant from Application 11710526.2, dated Apr. 23, 2014.
European Intention to Grant from Application No. 14705056.1, dated Apr. 18, 2017.
Extended European Search Report from Application 16180991.8 dated Jan. 26, 2017.
Ganz et al., JNCI, vol. 94, No. 1, 2002, pp. 39-49.
Gao et al., Chinese Medical Journal, vol. 121, No. 16, 2008, pp. 1563-1568.
Gianni et al., JCO, vol. 27, 2009, pp. 2474-2481.
Glas et al., BMC Genomics, vol. 7, No. 278, 2006, pp. 1-10.
Greenbaum et al., Genome Biology, vol. 4, No. 117, 2003, pp. 1-8.
Habel et al., Breast Cancer Research, vol. 8, 2006, pp. 1-15.
Hess et al., J Clin Oncol., vol. 24, No. 26, 2006, pp. 4236-4244.
International Preliminary Report on Patentability and Written Opinion from Application No. PCT/EP2009/057418, dated Dec. 18, 2010.
International Preliminary Report on Patentability and Written Opinion from Application No. PCT/EP2009/057426, dated Dec. 18, 2010.
International Preliminary Report on Patentability and Written Opinion from Application No. PCT/EP2011/054855, dated Oct. 2, 2012.
International Preliminary Report on Patentability and Written Opinion from Application No. PCT/EP2014/051937, dated Aug. 4, 2015.
International Preliminary Report on Patentability and Written Opinion from Application No. PCT/EP2015/052081, dated Aug. 18, 2016.
International Preliminary Report on Patentability and Written Opinion from Application No. PCT/US2010/024603, dated Sep. 28, 2010.
International Search Report and Written Opinion from Application No. PCT/EP2017/055601, dated Apr. 18, 2017.
International Search Report from Application No. PCT/EP2009/057418, dated Nov. 5, 2009.
International Search Report from Application No. PCT/EP2009/057426, dated Nov. 2, 2009.
International Search Report from Application No. PCT/EP2014/051937, dated Apr. 1, 2014.
Korean Communication from Application No. 10-2012-7025899, dated Aug. 22, 2017.
Liu et al., PLOS One, vol. 7, No. 5, 2012, pp. e36383.
Lu et al., Clinical Cancer Research, vol. 10, 2004, pp. 3291-3300.
Martin et al., PLOS One, vol. 3, No. 8, 2008, pp. e2994-1-e2994-9.
May et al., Science, vol. 241, 1988, pp. 1441-1449.
Canadian Office Action from Application No. 2,793,133 dated Feb. 26, 2018, 4 pages.
European Communication from Application No. 15702464.7, dated Jun. 8, 2018, 5 pages.

* cited by examiner

SEQUENCE LISTING

```
<160> NUMBER OF SEQ ID NOS: 141

<210> SEQ ID NO 1
<211> LENGTH: 22
<212> TYPE: DNA
<213> ORGANISM: Homo sapiens

<400> SEQUENCE: 1
tcgccctaag aggctcttcc tc                                        22

<210> SEQ ID NO 2
<211> LENGTH: 23
<212> TYPE: DNA
<213> ORGANISM: Homo sapiens

<400> SEQUENCE: 2
ggcaacttga ggtctgactt ttg                                       23

<210> SEQ ID NO 3
<211> LENGTH: 22
<212> TYPE: DNA
<213> ORGANISM: Homo sapiens

<400> SEQUENCE: 3
ggtcagctca caagtggtgt ga                                        22

<210> SEQ ID NO 4
<211> LENGTH: 22
<212> TYPE: DNA
<213> ORGANISM: Homo sapiens

<400> SEQUENCE: 4
```

```
ttgtcctttc cccctccgt gc                                        22
```

<210> SEQ ID NO 5
<211> LENGTH: 23
<212> TYPE: DNA
<213> ORGANISM: Homo sapiens

<400> SEQUENCE: 5

```
ccccaagagc tgttaggtat caa                                      23
```

<210> SEQ ID NO 6
<211> LENGTH: 24
<212> TYPE: DNA
<213> ORGANISM: Homo sapiens

<400> SEQUENCE: 6

```
tcaatgacat gatctcaacc agaa                                     24
```

<210> SEQ ID NO 7
<211> LENGTH: 27
<212> TYPE: DNA
<213> ORGANISM: Homo sapiens

<400> SEQUENCE: 7

```
catcagctct caactcctgg tttaaca                                  27
```

<210> SEQ ID NO 8
<211> LENGTH: 26
<212> TYPE: DNA
<213> ORGANISM: Homo sapiens

<400> SEQUENCE: 8

```
actcactaat ggaaaacgga aagatc                                   26
```

<210> SEQ ID NO 9
<211> LENGTH: 24
<212> TYPE: DNA
<213> ORGANISM: Homo sapiens

<400> SEQUENCE: 9

```
tcaccttcga tttgattcac agtt                                     24
```

<210> SEQ ID NO 10
<211> LENGTH: 24
<212> TYPE: DNA
<213> ORGANISM: Homo sapiens

<400> SEQUENCE: 10

```
tgggaggaag gcaaggtgct catc                                     24
```

<210> SEQ ID NO 11
<211> LENGTH: 20
<212> TYPE: DNA
<213> ORGANISM: Homo sapiens

<400> SEQUENCE: 11

```
tgtgccaacg agaccaagac                                          20
```

<210> SEQ ID NO 12
<211> LENGTH: 21
<212> TYPE: DNA
<213> ORGANISM: Homo sapiens

<400> SEQUENCE: 12

-continued tcgtgctcaa aggagtcatc a					21

<210> SEQ ID NO 13
<211> LENGTH: 21
<212> TYPE: DNA
<213> ORGANISM: Homo sapiens

<400> SEQUENCE: 13
ccgtcagcct gtgctaggca t					21

<210> SEQ ID NO 14
<211> LENGTH: 20
<212> TYPE: DNA
<213> ORGANISM: Homo sapiens

<400> SEQUENCE: 14
aatctggagg caaggttcga					20

<210> SEQ ID NO 15
<211> LENGTH: 21
<212> TYPE: DNA
<213> ORGANISM: Homo sapiens

<400> SEQUENCE: 15
tctggatttg cctcctgtga a					21

<210> SEQ ID NO 16
<211> LENGTH: 28
<212> TYPE: DNA
<213> ORGANISM: Homo sapiens

<400> SEQUENCE: 16
agccagatga cgaccccata gaggaaca				28

<210> SEQ ID NO 17
<211> LENGTH: 23
<212> TYPE: DNA
<213> ORGANISM: Homo sapiens

<400> SEQUENCE: 17
cccagtgttt cttctgcttc aag				23

<210> SEQ ID NO 18
<211> LENGTH: 20
<212> TYPE: DNA
<213> ORGANISM: Homo sapiens

<400> SEQUENCE: 18
caaccggacg aatgctttt					20

<210> SEQ ID NO 19
<211> LENGTH: 27
<212> TYPE: DNA
<213> ORGANISM: Homo sapiens

<400> SEQUENCE: 19
actgactttc cttctggagc aggtggc				27

<210> SEQ ID NO 20
<211> LENGTH: 24
<212> TYPE: DNA
<213> ORGANISM: Homo sapiens -continued

```
<400> SEQUENCE: 20
tccaagcatg tattccagac ttgt                                        24

<210> SEQ ID NO 21
<211> LENGTH: 20
<212> TYPE: DNA
<213> ORGANISM: Homo sapiens

<400> SEQUENCE: 21
tgcccacagc ctcttttct                                              20

<210> SEQ ID NO 22
<211> LENGTH: 21
<212> TYPE: DNA
<213> ORGANISM: Homo sapiens

<400> SEQUENCE: 22
ccacggccac cgaagaggca c                                           21

<210> SEQ ID NO 23
<211> LENGTH: 21
<212> TYPE: DNA
<213> ORGANISM: Homo sapiens

<400> SEQUENCE: 23
cgctcgtgct catctcctac t                                           21

<210> SEQ ID NO 24
<211> LENGTH: 24
<212> TYPE: DNA
<213> ORGANISM: Homo sapiens

<400> SEQUENCE: 24
cccagtgcac ataaaaggta tgtc                                        24

<210> SEQ ID NO 25
<211> LENGTH: 22
<212> TYPE: DNA
<213> ORGANISM: Homo sapiens

<400> SEQUENCE: 25
ccacagcagg gtttcaggtt cc                                          22

<210> SEQ ID NO 26
<211> LENGTH: 19
<212> TYPE: DNA
<213> ORGANISM: Homo sapiens

<400> SEQUENCE: 26
gccactaccc cctcctgaa                                              19

<210> SEQ ID NO 27
<211> LENGTH: 22
<212> TYPE: DNA
<213> ORGANISM: Homo sapiens

<400> SEQUENCE: 27
tcaccttgcc aacagttctg at                                          22

<210> SEQ ID NO 28
<211> LENGTH: 20
<212> TYPE: DNA
<213> ORGANISM: Homo sapiens
```

```
<400> SEQUENCE: 28
agggcatcgc catcatcgtc                                              20

<210> SEQ ID NO 29
<211> LENGTH: 19
<212> TYPE: DNA
<213> ORGANISM: Homo sapiens

<400> SEQUENCE: 29
gtcaccggct tcgtcttca                                               19

<210> SEQ ID NO 30
<211> LENGTH: 19
<212> TYPE: DNA
<213> ORGANISM: Homo sapiens

<400> SEQUENCE: 30
caggtccacg gcagtctgt                                               19

<210> SEQ ID NO 31
<211> LENGTH: 21
<212> TYPE: DNA
<213> ORGANISM: Homo sapiens

<400> SEQUENCE: 31
tcttttcagc aacccggtcc a                                            21

<210> SEQ ID NO 32
<211> LENGTH: 22
<212> TYPE: DNA
<213> ORGANISM: Homo sapiens

<400> SEQUENCE: 32
aaggcttctt attcgggtgt ga                                           22

<210> SEQ ID NO 33
<211> LENGTH: 22
<212> TYPE: DNA
<213> ORGANISM: Homo sapiens

<400> SEQUENCE: 33
tggatggctg tatctcccag ta                                           22

<210> SEQ ID NO 34
<211> LENGTH: 19
<212> TYPE: DNA
<213> ORGANISM: Homo sapiens

<400> SEQUENCE: 34
tgagcgccca ccctctcga                                               19

<210> SEQ ID NO 35
<211> LENGTH: 18
<212> TYPE: DNA
<213> ORGANISM: Homo sapiens

<400> SEQUENCE: 35
gggctctgct tcccgatt                                                18

<210> SEQ ID NO 36
<211> LENGTH: 24
<212> TYPE: DNA
```

```
<213> ORGANISM: Homo sapiens

<400> SEQUENCE: 36
agtcataggg caagcagaaa attc                                      24

<210> SEQ ID NO 37
<211> LENGTH: 26
<212> TYPE: DNA
<213> ORGANISM: Homo sapiens

<400> SEQUENCE: 37
caggatacct aatccctctc acgcag                                    26

<210> SEQ ID NO 38
<211> LENGTH: 22
<212> TYPE: DNA
<213> ORGANISM: Homo sapiens

<400> SEQUENCE: 38
aaatgtctcc gcaaccttgt tc                                        22

<210> SEQ ID NO 39
<211> LENGTH: 17
<212> TYPE: DNA
<213> ORGANISM: Homo sapiens

<400> SEQUENCE: 39
ctgcccccag ggatgag                                              17

<210> SEQ ID NO 40
<211> LENGTH: 24
<212> TYPE: DNA
<213> ORGANISM: Homo sapiens

<400> SEQUENCE: 40
tgaagcggga ggactttttg taaa                                      24

<210> SEQ ID NO 41
<211> LENGTH: 24
<212> TYPE: DNA
<213> ORGANISM: Homo sapiens

<400> SEQUENCE: 41
cgatgagagt gttttatcca tgca                                      24

<210> SEQ ID NO 42
<211> LENGTH: 19
<212> TYPE: DNA
<213> ORGANISM: Homo sapiens

<400> SEQUENCE: 42
gctgaggctg ggctcttct                                            19

<210> SEQ ID NO 43
<211> LENGTH: 19
<212> TYPE: DNA
<213> ORGANISM: Homo sapiens

<400> SEQUENCE: 43
atgccctttt gccgatgca                                            19

<210> SEQ ID NO 44
<211> LENGTH: 24
```

```
<212> TYPE: DNA
<213> ORGANISM: Homo sapiens

<400> SEQUENCE: 44
gccaaattgt gtttgatgga ttaa                                           24

<210> SEQ ID NO 45
<211> LENGTH: 27
<212> TYPE: DNA
<213> ORGANISM: Homo sapiens

<400> SEQUENCE: 45
gacaaaaccg agtcacatca gtaatag                                        27

<210> SEQ ID NO 46
<211> LENGTH: 25
<212> TYPE: DNA
<213> ORGANISM: Homo sapiens

<400> SEQUENCE: 46
tgcacagcct tttgatttcc ccgat                                          25

<210> SEQ ID NO 47
<211> LENGTH: 22
<212> TYPE: DNA
<213> ORGANISM: Homo sapiens

<400> SEQUENCE: 47
cgggaagcac catctctaac tc                                             22

<210> SEQ ID NO 48
<211> LENGTH: 24
<212> TYPE: DNA
<213> ORGANISM: Homo sapiens

<400> SEQUENCE: 48
ttcatgtcca gcagctagtt tttt                                           24

<210> SEQ ID NO 49
<211> LENGTH: 21
<212> TYPE: DNA
<213> ORGANISM: Homo sapiens

<400> SEQUENCE: 49
caagtcagca aacacgcaaa a                                              21

<210> SEQ ID NO 50
<211> LENGTH: 24
<212> TYPE: DNA
<213> ORGANISM: Homo sapiens

<400> SEQUENCE: 50
catgcacgaa ctaatcaaaa atgc                                           24

<210> SEQ ID NO 51
<211> LENGTH: 27
<212> TYPE: DNA
<213> ORGANISM: Homo sapiens

<400> SEQUENCE: 51
acattattcg aggtttctct ttaatgc                                        27

<210> SEQ ID NO 52
```

-continued

```
<211> LENGTH: 24
<212> TYPE: DNA
<213> ORGANISM: Homo sapiens

<400> SEQUENCE: 52
caagctccac cttccaaagg acct                                              24

<210> SEQ ID NO 53
<211> LENGTH: 23
<212> TYPE: DNA
<213> ORGANISM: Homo sapiens

<400> SEQUENCE: 53
ccctgaatcc ataaaggcat acc                                               23

<210> SEQ ID NO 54
<211> LENGTH: 24
<212> TYPE: DNA
<213> ORGANISM: Homo sapiens

<400> SEQUENCE: 54
cagcttcgtt tttccctact tttt                                              24

<210> SEQ ID NO 55
<211> LENGTH: 22
<212> TYPE: DNA
<213> ORGANISM: Homo sapiens

<400> SEQUENCE: 55
tccgagcgct ggattgcatg ag                                                22

<210> SEQ ID NO 56
<211> LENGTH: 25
<212> TYPE: DNA
<213> ORGANISM: Homo sapiens

<400> SEQUENCE: 56
gcaccagtta cacaaggact tcttt                                             25

<210> SEQ ID NO 57
<211> LENGTH: 21
<212> TYPE: DNA
<213> ORGANISM: Homo sapiens

<400> SEQUENCE: 57
tctctatgcg gcatccttct c                                                 21

<210> SEQ ID NO 58
<211> LENGTH: 23
<212> TYPE: DNA
<213> ORGANISM: Homo sapiens

<400> SEQUENCE: 58
agactatttg cacactgccg cct                                               23

<210> SEQ ID NO 59
<211> LENGTH: 26
<212> TYPE: DNA
<213> ORGANISM: Homo sapiens

<400> SEQUENCE: 59
gtggctcaaa ggataatatc aaacac                                            26
```

-continued

```
<210> SEQ ID NO 60
<211> LENGTH: 22
<212> TYPE: DNA
<213> ORGANISM: Homo sapiens

<400> SEQUENCE: 60
accttgctca ggtcaactgg tt                                            22

<210> SEQ ID NO 61
<211> LENGTH: 26
<212> TYPE: DNA
<213> ORGANISM: Homo sapiens

<400> SEQUENCE: 61
ccttcatatc ccctcagcag agatgg                                        26

<210> SEQ ID NO 62
<211> LENGTH: 24
<212> TYPE: DNA
<213> ORGANISM: Homo sapiens

<400> SEQUENCE: 62
ccttcattaa caggagaaat gcaa                                          24

<210> SEQ ID NO 63
<211> LENGTH: 22
<212> TYPE: DNA
<213> ORGANISM: Homo sapiens

<400> SEQUENCE: 63
attgagctcg tggacaggct ta                                            22

<210> SEQ ID NO 64
<211> LENGTH: 30
<212> TYPE: DNA
<213> ORGANISM: Homo sapiens

<400> SEQUENCE: 64
tcctgaacaa atgaatcgca tgtcctacaa                                    30

<210> SEQ ID NO 65
<211> LENGTH: 26
<212> TYPE: DNA
<213> ORGANISM: Homo sapiens

<400> SEQUENCE: 65
atttgttggc acaccttatt acatgt                                        26

<210> SEQ ID NO 66
<211> LENGTH: 21
<212> TYPE: DNA
<213> ORGANISM: Homo sapiens

<400> SEQUENCE: 66
aagcagccca atgaccagat a                                             21

<210> SEQ ID NO 67
<211> LENGTH: 25
<212> TYPE: DNA
<213> ORGANISM: Homo sapiens

<400> SEQUENCE: 67
aaatactaaa atgcgccggc aatga                                         25
```

<210> SEQ ID NO 68
<211> LENGTH: 20
<212> TYPE: DNA
<213> ORGANISM: Homo sapiens

<400> SEQUENCE: 68
gggcgtgaac ctcaccagta                                         20

<210> SEQ ID NO 69
<211> LENGTH: 25
<212> TYPE: DNA
<213> ORGANISM: Homo sapiens

<400> SEQUENCE: 69
cttcggccct tagtgtaatg atatc                                   25

<210> SEQ ID NO 70
<211> LENGTH: 24
<212> TYPE: DNA
<213> ORGANISM: Homo sapiens

<400> SEQUENCE: 70
ttgatagaaa cgctgtgagc tcga                                    24

<210> SEQ ID NO 71
<211> LENGTH: 22
<212> TYPE: DNA
<213> ORGANISM: Homo sapiens

<400> SEQUENCE: 71
agctcatcaa ggcaattggt tt                                      22

<210> SEQ ID NO 72
<211> LENGTH: 28
<212> TYPE: DNA
<213> ORGANISM: Homo sapiens

<400> SEQUENCE: 72
acaagatcat gcaagttatc aagaagtt                                28

<210> SEQ ID NO 73
<211> LENGTH: 25
<212> TYPE: DNA
<213> ORGANISM: Homo sapiens

<400> SEQUENCE: 73
tgcatggtgg ttaaaactta cctca                                   25

<210> SEQ ID NO 74
<211> LENGTH: 23
<212> TYPE: DNA
<213> ORGANISM: Homo sapiens

<400> SEQUENCE: 74
tgcttgcagt tcaaacagaa ttg                                     23

<210> SEQ ID NO 75
<211> LENGTH: 23
<212> TYPE: DNA
<213> ORGANISM: Homo sapiens

<400> SEQUENCE: 75
caccttgtag agggatgctg cta                                     23

```
<210> SEQ ID NO 76
<211> LENGTH: 23
<212> TYPE: DNA
<213> ORGANISM: Homo sapiens

<400> SEQUENCE: 76
cagaaagtgg ccatgccacc ctg                                              23

<210> SEQ ID NO 77
<211> LENGTH: 23
<212> TYPE: DNA
<213> ORGANISM: Homo sapiens

<400> SEQUENCE: 77
tgggaagaca tgaatgcaca cta                                              23

<210> SEQ ID NO 78
<211> LENGTH: 21
<212> TYPE: DNA
<213> ORGANISM: Homo sapiens

<400> SEQUENCE: 78
ggaggttggg ctttagctga a                                                21

<210> SEQ ID NO 79
<211> LENGTH: 21
<212> TYPE: DNA
<213> ORGANISM: Homo sapiens

<400> SEQUENCE: 79
cactgccggt cacccacacc a                                                21

<210> SEQ ID NO 80
<211> LENGTH: 23
<212> TYPE: DNA
<213> ORGANISM: Homo sapiens

<400> SEQUENCE: 80
ctgaggagca cagaacctca act                                              23

<210> SEQ ID NO 81
<211> LENGTH: 25
<212> TYPE: DNA
<213> ORGANISM: Homo sapiens

<400> SEQUENCE: 81
cgaactcggt acatgtctga tacaa                                            25

<210> SEQ ID NO 82
<211> LENGTH: 22
<212> TYPE: DNA
<213> ORGANISM: Homo sapiens

<400> SEQUENCE: 82
tcggtctgct ggtctccgct cc                                               22

<210> SEQ ID NO 83
<211> LENGTH: 26
<212> TYPE: DNA
<213> ORGANISM: Homo sapiens

<400> SEQUENCE: 83
```
ctgattgaag atcattttca acatca                                    26

<210> SEQ ID NO 84
<211> LENGTH: 20
<212> TYPE: DNA
<213> ORGANISM: Homo sapiens

<400> SEQUENCE: 84
gacggccatt cagcttatgg                                           20

<210> SEQ ID NO 85
<211> LENGTH: 22
<212> TYPE: DNA
<213> ORGANISM: Homo sapiens

<400> SEQUENCE: 85
ttggcttctg gacaccctca ca                                        22

<210> SEQ ID NO 86
<211> LENGTH: 22
<212> TYPE: DNA
<213> ORGANISM: Homo sapiens

<400> SEQUENCE: 86
gagttgtggc ctctaccatt gc                                        22

<210> SEQ ID NO 87
<211> LENGTH: 20
<212> TYPE: DNA
<213> ORGANISM: Homo sapiens

<400> SEQUENCE: 87
gagcgggaac cttgggatag                                           20

<210> SEQ ID NO 88
<211> LENGTH: 23
<212> TYPE: DNA
<213> ORGANISM: Homo sapiens

<400> SEQUENCE: 88
actgagaatc tccacccggc gca                                       23

<210> SEQ ID NO 89
<211> LENGTH: 21
<212> TYPE: DNA
<213> ORGANISM: Homo sapiens

<400> SEQUENCE: 89
tcgccaactg gataaattgg a                                         21

<210> SEQ ID NO 90
<211> LENGTH: 22
<212> TYPE: DNA
<213> ORGANISM: Homo sapiens

<400> SEQUENCE: 90
gaatgtgcgg aatctgtttg ag                                        22

<210> SEQ ID NO 91
<211> LENGTH: 26
<212> TYPE: DNA
<213> ORGANISM: Homo sapiens

<400> SEQUENCE: 91

```
accgattccg ctacattcca cccaac                                        26
```

<210> SEQ ID NO 92
<211> LENGTH: 22
<212> TYPE: DNA
<213> ORGANISM: Homo sapiens

<400> SEQUENCE: 92

```
agaaattggc ttcctgctca ag                                            22
```

<210> SEQ ID NO 93
<211> LENGTH: 25
<212> TYPE: DNA
<213> ORGANISM: Homo sapiens

<400> SEQUENCE: 93

```
aaaaccaact tcccaaaaat tctct                                         25
```

<210> SEQ ID NO 94
<211> LENGTH: 31
<212> TYPE: DNA
<213> ORGANISM: Homo sapiens

<400> SEQUENCE: 94

```
ctagagggtt ccaggtccca tacgtgacat a                                  31
```

<210> SEQ ID NO 95
<211> LENGTH: 24
<212> TYPE: DNA
<213> ORGANISM: Homo sapiens

<400> SEQUENCE: 95

```
tgtggattca gttcaagtcc aatg                                          24
```

<210> SEQ ID NO 96
<211> LENGTH: 27
<212> TYPE: DNA
<213> ORGANISM: Homo sapiens

<400> SEQUENCE: 96

```
ccatctcgaa ctatgtcttc aatgagt                                       27
```

<210> SEQ ID NO 97
<211> LENGTH: 20
<212> TYPE: DNA
<213> ORGANISM: Homo sapiens

<400> SEQUENCE: 97

```
tgggaggcat gcaacgcgtg                                               20
```

<210> SEQ ID NO 98
<211> LENGTH: 26
<212> TYPE: DNA
<213> ORGANISM: Homo sapiens

<400> SEQUENCE: 98

```
aggtcttact aagcagtccc atctct                                        26
```

<210> SEQ ID NO 99
<211> LENGTH: 18
<212> TYPE: DNA
<213> ORGANISM: Homo sapiens

<400> SEQUENCE: 99
cgaccggcac ctgaactc                                                      18

<210> SEQ ID NO 100
<211> LENGTH: 29
<212> TYPE: DNA
<213> ORGANISM: Homo sapiens

<400> SEQUENCE: 100
tatgcgtctc ccaaaagaag aacacctcg                                          29

<210> SEQ ID NO 101
<211> LENGTH: 21
<212> TYPE: DNA
<213> ORGANISM: Homo sapiens

<400> SEQUENCE: 101
gcaagcttcc ttcctccttc a                                                  21

<210> SEQ ID NO 102
<211> LENGTH: 31
<212> TYPE: DNA
<213> ORGANISM: Homo sapiens

<400> SEQUENCE: 102
cctttagcag ttttctccat agttttatat c                                       31

<210> SEQ ID NO 103
<211> LENGTH: 27
<212> TYPE: DNA
<213> ORGANISM: Homo sapiens

<400> SEQUENCE: 103
caacaccacc actaacaggc acacgtc                                            27

<210> SEQ ID NO 104
<211> LENGTH: 22
<212> TYPE: DNA
<213> ORGANISM: Homo sapiens

<400> SEQUENCE: 104
ggcatggaca agatgttctt ga                                                 22

<210> SEQ ID NO 105
<211> LENGTH: 22
<212> TYPE: DNA
<213> ORGANISM: Homo sapiens

<400> SEQUENCE: 105
cctccttgtc gccagtttta ct                                                 22

<210> SEQ ID NO 106
<211> LENGTH: 28
<212> TYPE: DNA
<213> ORGANISM: Homo sapiens

<400> SEQUENCE: 106
cagatcagga ccaagatggt tcccacat                                           28

<210> SEQ ID NO 107
<211> LENGTH: 22
<212> TYPE: DNA
<213> ORGANISM: Homo sapiens

<400> SEQUENCE: 107
cattgaagac gcttcgttat gg                                     22

<210> SEQ ID NO 108
<211> LENGTH: 27
<212> TYPE: DNA
<213> ORGANISM: Homo sapiens

<400> SEQUENCE: 108
ccagttgtga tggataaaat taatcag                                27

<210> SEQ ID NO 109
<211> LENGTH: 27
<212> TYPE: DNA
<213> ORGANISM: Homo sapiens

<400> SEQUENCE: 109
tgctgtctca ctaccggcca ttctacg                                27

<210> SEQ ID NO 110
<211> LENGTH: 21
<212> TYPE: DNA
<213> ORGANISM: Homo sapiens

<400> SEQUENCE: 110
tggaaatctg gcaagcagac t                                      21

<210> SEQ ID NO 111
<211> LENGTH: 20
<212> TYPE: DNA
<213> ORGANISM: Homo sapiens

<400> SEQUENCE: 111
caatcccgtt gcctttgttg                                        20

<210> SEQ ID NO 112
<211> LENGTH: 25
<212> TYPE: DNA
<213> ORGANISM: Homo sapiens

<400> SEQUENCE: 112
tgaacacaca tgctgccgag ctctg                                  25

<210> SEQ ID NO 113
<211> LENGTH: 27
<212> TYPE: DNA
<213> ORGANISM: Homo sapiens

<400> SEQUENCE: 113
cttctaggag aacccaacat tgatagt                                27

<210> SEQ ID NO 114
<211> LENGTH: 27
<212> TYPE: DNA
<213> ORGANISM: Homo sapiens

<400> SEQUENCE: 114
gtttcttgca ggtacttctt aaaagct                                27

<210> SEQ ID NO 115
<211> LENGTH: 30
<212> TYPE: DNA

<213> ORGANISM: Homo sapiens

<400> SEQUENCE: 115
tattcacatc ccctcagttg cagtgaattg                              30

<210> SEQ ID NO 116
<211> LENGTH: 27
<212> TYPE: DNA
<213> ORGANISM: Homo sapiens

<400> SEQUENCE: 116
ctgtggctct taatttattg cataatg                                 27

<210> SEQ ID NO 117
<211> LENGTH: 26
<212> TYPE: DNA
<213> ORGANISM: Homo sapiens

<400> SEQUENCE: 117
ttagtgcttt ttgctttcaa gatctt                                  26

<210> SEQ ID NO 118
<211> LENGTH: 23
<212> TYPE: DNA
<213> ORGANISM: Homo sapiens

<400> SEQUENCE: 118
tctcaccttg accctcagcc aag                                     23

<210> SEQ ID NO 119
<211> LENGTH: 26
<212> TYPE: DNA
<213> ORGANISM: Homo sapiens

<400> SEQUENCE: 119
acatttgaca aatttccctt aggatt                                  26

<210> SEQ ID NO 120
<211> LENGTH: 20
<212> TYPE: DNA
<213> ORGANISM: Homo sapiens

<400> SEQUENCE: 120
ccaggacgca gctttaccaa                                         20

<210> SEQ ID NO 121
<211> LENGTH: 20
<212> TYPE: DNA
<213> ORGANISM: Homo sapiens

<400> SEQUENCE: 121
caccagccac caggccccag                                         20

<210> SEQ ID NO 122
<211> LENGTH: 18
<212> TYPE: DNA
<213> ORGANISM: Homo sapiens

<400> SEQUENCE: 122
tcctggaccg gcaagatc                                           18

<210> SEQ ID NO 123
<211> LENGTH: 21

```
<212> TYPE: DNA
<213> ORGANISM: Homo sapiens

<400> SEQUENCE: 123
taggccaggc acttcagttt c                                      21

<210> SEQ ID NO 124
<211> LENGTH: 22
<212> TYPE: DNA
<213> ORGANISM: Homo sapiens

<400> SEQUENCE: 124
tcgcgtctcg gaaaccggta gc                                     22

<210> SEQ ID NO 125
<211> LENGTH: 20
<212> TYPE: DNA
<213> ORGANISM: Homo sapiens

<400> SEQUENCE: 125
gagcgagctg agtggttgtg                                        20

<210> SEQ ID NO 126
<211> LENGTH: 21
<212> TYPE: DNA
<213> ORGANISM: Homo sapiens

<400> SEQUENCE: 126
agtcagttgg tcagccatgc t                                      21

<210> SEQ ID NO 127
<211> LENGTH: 27
<212> TYPE: DNA
<213> ORGANISM: Homo sapiens

<400> SEQUENCE: 127
cctgccaatc ccgatgaaat tggaaat                                27

<210> SEQ ID NO 128
<211> LENGTH: 21
<212> TYPE: DNA
<213> ORGANISM: Homo sapiens

<400> SEQUENCE: 128
tgagtgtccc ccggtatctt c                                      21

<210> SEQ ID NO 129
<211> LENGTH: 21
<212> TYPE: DNA
<213> ORGANISM: Homo sapiens

<400> SEQUENCE: 129
tcagccgctt tcagattttc a                                      21

<210> SEQ ID NO 130
<211> LENGTH: 26
<212> TYPE: DNA
<213> ORGANISM: Homo sapiens

<400> SEQUENCE: 130
accctgctga ccttcttcca ttccgt                                 26

<210> SEQ ID NO 131
```

```
<211> LENGTH: 22
<212> TYPE: DNA
<213> ORGANISM: Homo sapiens

<400> SEQUENCE: 131
agaaattggc ttcctgctca ag                                              22

<210> SEQ ID NO 132
<211> LENGTH: 25
<212> TYPE: DNA
<213> ORGANISM: Homo sapiens

<400> SEQUENCE: 132
aaaaccaact tcccaaaaat tctct                                           25

<210> SEQ ID NO 133
<211> LENGTH: 23
<212> TYPE: DNA
<213> ORGANISM: Homo sapiens

<400> SEQUENCE: 133
tgcttccaca agaaccgcga gga                                             23

<210> SEQ ID NO 134
<211> LENGTH: 20
<212> TYPE: DNA
<213> ORGANISM: Homo sapiens

<400> SEQUENCE: 134
cgagccgacc atgtcttcat                                                 20

<210> SEQ ID NO 135
<211> LENGTH: 21
<212> TYPE: DNA
<213> ORGANISM: Homo sapiens

<400> SEQUENCE: 135
aagcccaaaa agctgaaggt t                                               21

<210> SEQ ID NO 136
<211> LENGTH: 22
<212> TYPE: DNA
<213> ORGANISM: Homo sapiens

<400> SEQUENCE: 136
aagttcttcc aaatggtcgg cc                                              22

<210> SEQ ID NO 137
<211> LENGTH: 19
<212> TYPE: DNA
<213> ORGANISM: Homo sapiens

<400> SEQUENCE: 137
ccgactcctt cgaccacaa                                                  19

<210> SEQ ID NO 138
<211> LENGTH: 23
<212> TYPE: DNA
<213> ORGANISM: Homo sapiens

<400> SEQUENCE: 138
catcatccgc actcttttte ttc                                             23
```

```
-continued

<210> SEQ ID NO 139
<211> LENGTH: 18
<212> TYPE: DNA
<213> ORGANISM: Homo sapiens

<400> SEQUENCE: 139
tggctggcgg tgcctgga                                                 18

<210> SEQ ID NO 140
<211> LENGTH: 21
<212> TYPE: DNA
<213> ORGANISM: Homo sapiens

<400> SEQUENCE: 140
tgtggttcct gcatgaagac a                                             21

<210> SEQ ID NO 141
<211> LENGTH: 24
<212> TYPE: DNA
<213> ORGANISM: Homo sapiens

<400> SEQUENCE: 141
gtgacagcgg aagtggtatt gtac                                          24
```

METHOD FOR BREAST CANCER RECURRENCE PREDICTION UNDER ENDOCRINE TREATMENT

CROSS-REFERENCE TO RELATED APPLICATIONS

This application is a continuation of U.S. Ser. No. 13/638,360, filed Nov. 21, 2012, which is a U.S. National Stage Patent of PCT Application No. PCT/EP2011/054855, filed Mar. 29, 2011, which claims the benefit of European Patent Application No. 10158561.0, filed Mar. 31, 2010, all of which are hereby incorporated by reference in their entireties.

TECHNICAL FIELD

The present invention relates to methods, kits and systems for the prognosis of the disease outcome of breast cancer. More specific, the present invention relates to the prognosis of breast cancer based on measurements of the expression levels of marker genes in tumor samples of breast cancer patients.

BACKGROUND OF THE INVENTION

Breast cancer is one of the leading causes of cancer death in women in western countries. More specifically breast cancer claims the lives of approximately 40,000 women and is diagnosed in approximately 200,000 women annually in the United States alone. Over the last few decades, adjuvant systemic therapy has led to markedly improved survival in early breast cancer. This clinical experience has led to consensus recommendations offering adjuvant systemic therapy for the vast majority of breast cancer patients (EBCAG). In breast cancer a multitude of treatment options are available which can be applied in addition to the routinely performed surgical removal of the tumor and subsequent radiation of the tumor bed. Three main and conceptually different strategies are endocrine treatment, chemotherapy and treatment with targeted therapies. Prerequisite for treatment with endocrine agents is expression of hormone receptors in the tumor tissue i.e. either estrogen receptor, progesterone receptor or both. Several endocrine agents with different mode of action and differences in disease outcome when tested in large patient cohorts are available. Tamoxifen has been the mainstay of endocrine treatment for the last three decades. Large clinical trials showed that tamoxifen significantly reduced the risk of tumor recurrence. An additional treatment option is based on aromatase inhibitors which belong to a new endocrine drug class. In contrast to tamoxifen which is a competitive inhibitor of estrogen binding aromatase inhibitors block the production of estrogen itself thereby reducing the growth stimulus for estrogen receptor positive tumor cells. Still, some patients experience a relapse despite endocrine treatment and in particular these patients might benefit from additional therapeutic drugs. Chemotherapy with anthracyclines, taxanes and other agents have been shown to be efficient in reducing disease recurrence in estrogen receptor positive as well as estrogen receptor negative patients. The NSABP-20 study compared tamoxifen alone against tamoxifen plus chemotherapy in node negative estrogen receptor positive patients and showed that the combined treatment was more effective than tamoxifen alone. However, the IBCSG IX study comparing tamoxifen alone against tamoxifen plus chemotherapy failed to show any significant benefit for the addition of cytotoxic agents. Recently, a systemically administered antibody directed against the HER2/neu antigen on the surface of tumor cells have been shown to reduce the risk of recurrence several fold in a patients with Her2neu over expressing tumors. Yet, most if not all of the different drug treatments have numerous potential adverse effects which can severely impair patients' quality of life (Shapiro and Recht, 2001; Ganz et al., 2002). This makes it mandatory to select the treatment strategy on the basis of a careful risk assessment for the individual patient to avoid over-as well as under treatment. Since the benefit of chemotherapy is relatively large in HER2/neu positive and tumors characterized by absence of HER2/neu and estrogen receptor expression (basal type), compared to HER2/neu negative and estrogen receptor positive tumors (luminal type), the most challenging treatment decision concerns luminal tumors for which classical clinical factors like grading, tumor size or lymph node involvement do not provide a clear answer to the question whether to use chemotherapy or not. Newer molecular tools like a 21 gene assay, a genomic grade index assay and others have been developed to address this medical need.

Treatment guidelines are usually developed by renowned experts in the field. In Europe the St Gallen guidelines from the year 2009 recommend chemotherapy to patients with HER2 positive breast cancer as well as to patients with HER2 negative and ER negative disease. Uncertainty about the usefulness of chemotherapy arises in patients with HER2 negative and ER positive disease. In order to make a balanced treatment decision for the individual the likelihood of cancer recurrence is used as the most useful criteria. Clinical criteria like lypmph node status, tumor grading, tumor size and others are helpful since they provide information about the risk of recurrence. More recently, multi-gene assays have been shown to provide information superior or additional to the standard clinical risk factors. It is generally recognized, that proliferation markers seem to provide the dominant prognostic information. Prominent examples of those predictors are the Mammaprint test from Agendia, the Relapse Score from Veridex and the Genomic Grade Index, developed at the institute Jules Bordet and licensed to Ipsogen. All of these assays are based on determination of the expression levels of at least 70 genes and all have been developed for RNA not heavily degraded by formalin fixation and paraffin embedding, but isolated from fresh tissue (shipped in RNALater™). Another prominent multigene assay is the Recurrence Score test of Genomic Health Inc. The test determines the expression level of 16 cancer related genes and 5 reference genes after RNA extraction from formalin fixed and paraffin embedded tissue samples.

However, the current tools suffer from a lack of clinical validity and utility in the most important clinical risk group, i.e. those breast cancer patients of intermediate risk of recurrence based on standard clinical parameter. Therefore, better tools are needed to optimize treatment decisions based on patient prognosis. For the clinical utility of avoiding chemotherapy, a test with a high sensitivity and high negative predictive value is needed, in order not to undertreat a patient that eventually develops a distant metastasis after surgery. In regard to the continuing need for materials and methods useful in making clinical decisions on adjuvant therapy, the present invention fulfills the need for advanced methods for the prognosis of breast cancer on the basis of readily accessible clinical and experimental data.

DEFINITIONS

Unless defined otherwise, technical and scientific terms used herein have the same meaning as commonly understood by one of ordinary skill in the art to which this invention belongs.

The term "cancer" is not limited to any stage, grade, histomorphological feature, aggressivity, or malignancy of an affected tissue or cell aggregation.

The term "predicting an outcome" of a disease, as used herein, is meant to include both a prediction of an outcome of a patient undergoing a given therapy and a prognosis of a patient who is not treated. The term "predicting an outcome" may, in particular, relate to the risk of a patient developing metastasis, local recurrence or death.

The term "prediction", as used herein, relates to an individual assessment of the malignancy of a tumor, or to the expected survival rate (OAS, overall survival or DFS, disease free survival) of a patient, if the tumor is treated with a given therapy. In contrast thereto, the term "prognosis" relates to an individual assessment of the malignancy of a tumor, or to the expected survival rate (OAS, overall survival or DFS, disease free survival) of a patient, if the tumor remains untreated.

An "outcome" within the meaning of the present invention is a defined condition attained in the course of the disease. This disease outcome may e.g. be a clinical condition such as "recurrence of disease", "development of metastasis", "development of nodal metastasis", "development of distant metastasis", "survival", "death", "tumor remission rate", a disease stage or grade or the like.

A "risk" is understood to be a number related to the probability of a subject or a patient to develop or arrive at a certain disease outcome. The term "risk" in the context of the present invention is not meant to carry any positive or negative connotation with regard to a patient's wellbeing but merely refers to a probability or likelihood of an occurrence or development of a given condition.

The term "clinical data" relates to the entirety of available data and information concerning the health status of a patient including, but not limited to, age, sex, weight, menopausal/hormonal status, etiopathology data, anamnesis data, data obtained by in vitro diagnostic methods such as histopathology, blood or urine tests, data obtained by imaging methods, such as x-ray, computed tomography, MRI, PET, spect, ultrasound, electrophysiological data, genetic analysis, gene expression analysis, biopsy evaluation, intraoperative findings.

The term "node positive", "diagnosed as node positive", "node involvement" or "lymph node involvement" means a patient having previously been diagnosed with lymph node metastasis. It shall encompass both draining lymph node, near lymph node, and distant lymph node metastasis. This previous diagnosis itself shall not form part of the inventive method. Rather it is a precondition for selecting patients whose samples may be used for one embodiment of the present invention. This previous diagnosis may have been arrived at by any suitable method known in the art, including, but not limited to lymph node removal and pathological analysis, biopsy analysis, in-vitro analysis of biomarkers indicative for metastasis, imaging methods (e.g. computed tomography, X-ray, magnetic resonance imaging, ultrasound), and intraoperative findings.

In the context of the present invention a "biological sample" is a sample which is derived from or has been in contact with a biological organism. Examples for biological samples are: cells, tissue, body fluids, lavage fluid, smear samples, biopsy specimens, blood, urine, saliva, sputum, plasma, serum, cell culture supernatant, and others.

A "tumor sample" is a biological sample containing tumor cells, whether intact or degraded. The sample may be of any biological tissue or fluid. Such samples include, but are not limited to, sputum, blood, serum, plasma, blood cells (e.g., white cells), tissue, core or fine needle biopsy samples, cell-containing body fluids, urine, peritoneal fluid, and pleural fluid, liquor cerebrospinalis, tear fluid, or cells isolated therefrom. This may also include sections of tissues such as frozen or fixed sections taken for histological purposes or microdissected cells or extracellular parts thereof. A tumor sample to be analyzed can be tissue material from a neoplastic lesion taken by aspiration or punctuation, excision or by any other surgical method leading to biopsy or resected cellular material. Such comprises tumor cells or tumor cell fragments obtained from the patient. The cells may be found in a cell "smear" collected, for example, by a nipple aspiration, ductal lavage, fine needle biopsy or from provoked or spontaneous nipple discharge. In another embodiment, the sample is a body fluid. Such fluids include, for example, blood fluids, serum, plasma, lymph, ascitic fluids, gynecologic fluids, or urine but not limited to these fluids.

A "gene" is a set of segments of nucleic acid that contains the information necessary to produce a functional RNA product. A "gene product" is a biological molecule produced through transcription or expression of a gene, e.g. an mRNA, cDNA or the translated protein.

An "mRNA" is the transcribed product of a gene and shall have the ordinary meaning understood by a person skilled in the art. A "molecule derived from an mRNA" is a molecule which is chemically or enzymatically obtained from an mRNA template, such as cDNA.

The term "expression level" refers to a determined level of gene expression. This may be a determined level of gene expression as an absolute value or compared to a reference gene (e.g. a housekeeping gene), to the average of two or more reference genes, or to a computed average expression value (e.g. in DNA chip analysis) or to another informative gene without the use of a reference sample. The expression level of a gene may be measured directly, e.g. by obtaining a signal wherein the signal strength is correlated to the amount of mRNA transcripts of that gene or it may be obtained indirectly at a protein level, e.g. by immunohistochemistry, CISH, ELISA or RIA methods. The expression level may also be obtained by way of a competitive reaction to a reference sample. An expression value which is determined by measuring some physical parameter in an assay, e.g. fluorescence emission, may be assigned a numerical value which may be used for further processing of information.

A "reference pattern of expression levels", within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy individuals, diseased individuals, or diseased individuals having received a particular type of therapy, serving as a reference group, or individuals with good or bad outcome.

The term "mathematically combining expression levels", within the meaning of the invention shall be understood as deriving a numeric value from a determined expression level of a gene and applying an algorithm to one or more of such numeric values to obtain a combined numerical value or combined score.

An "algorithm" is a process that performs some sequence of operations to produce information.

A "score" is a numeric value that was derived by mathematically combining expression levels using an algorithm. It may also be derived from expression levels and other information, e.g. clinical data. A score may be related to the outcome of a patient's disease.

A "discriminant function" is a function of a set of variables used to classify an object or event. A discriminant function thus allows classification of a patient, sample or event into a category or a plurality of categories according to data or parameters available from said patient, sample or event. Such classification is a standard instrument of statistical analysis well known to the skilled person. E.g. a patient may be classified as "high risk" or "low risk", "high probability of metastasis" or "low probability of metastasis", "in need of treatment" or "not in need of treatment" according to data obtained from said patient, sample or event. Classification is not limited to "high vs. low", but may be performed into a plurality of categories, grading or the like. Classification shall also be understood in a wider sense as a discriminating score, where e.g. a higher score represents a higher likelihood of distant metastasis, e.g. the (overall) risk of a distant metastasis. Examples for discriminant functions which allow a classification include, but are not limited to functions defined by support vector machines (SVM), k-nearest neighbors (kNN), (naive) Bayes models, linear regression models or piecewise defined functions such as, for example, in subgroup discovery, in decision trees, in logical analysis of data (LAD) and the like. In a wider sense, continuous score values of mathematical methods or algorithms, such as correlation coefficients, projections, support vector machine scores, other similarity-based methods, combinations of these and the like are examples for illustrative purpose.

The term "therapy modality", "therapy mode", "regimen" as well as "therapy regimen" refers to a timely sequential or simultaneous administration of anti-tumor, and/or anti vascular, and/or immune stimulating, and/or blood cell proliferative agents, and/or radiation therapy, and/or hyperthermia, and/or hypothermia for cancer therapy. The administration of these can be performed in an adjuvant and/or neoadjuvant mode. The composition of such "protocol" may vary in the dose of the single agent, timeframe of application and frequency of administration within a defined therapy window. Currently various combinations of various drugs and/or physical methods, and various schedules are under investigation.

The term "cytotoxic chemotherapy" refers to various treatment modalities affecting cell proliferation and/or survival. The treatment may include administration of alkylating agents, antimetabolites, anthracyclines, plant alkaloids, topoisomerase inhibitors, and other antitumor agents, including monoclonal antibodies and kinase inhibitors. In particular, the cytotoxic treatment may relate to a taxane treatment. Taxanes are plant alkaloids which block cell division by preventing microtubule function. The prototype taxane is the natural product paclitaxel, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

The term "endocrine treatment" or "hormonal treatment" (sometimes also referred to as "anti-hormonal treatment") denotes a treatment which targets hormone signalling, e.g. hormone inhibition, hormone receptor inhibition, use of hormone receptor agonists or antagonists, use of scavenger- or orphan receptors, use of hormone derivatives and interference with hormone production. Particular examples are tamoxifene therapy which modulates signalling of the estrogen receptor, or aromatase treatment which interferes with steroid hormone production.

Tamoxifen is an orally active selective estrogen receptor modulator (SERM) that is used in the treatment of breast cancer and is currently the world's largest selling drug for that purpose. Tamoxifen is sold under the trade names Nolvadex, Istubal, and Valodex. However, the drug, even before its patent expiration, was and still is widely referred to by its generic name "tamoxifen." Tamoxifen and Tamoxifen derivatives competitively bind to estrogen receptors on tumors and other tissue targets, producing a nuclear complex that decreases RNA synthesis and inhibits estrogen effects.

Steroid receptors are intracellular receptors (typically cytoplasmic) that perform signal transduction for steroid hormones. Examples include type I Receptors, in particular sex hormone receptors, e.g. androgen receptor, estrogen receptor, progesterone receptor; Glucocorticoid receptor, mineralocorticoid receptor; and type II Receptors, e.g. vitamin A receptor, vitamin D receptor, retinoid receptor, thyroid hormone receptor.

The term "hybridization-based method", as used herein, refers to methods imparting a process of combining complementary, single-stranded nucleic acids or nucleotide analogues into a single double stranded molecule. Nucleotides or nucleotide analogues will bind to their complement under normal conditions, so two perfectly complementary strands will bind to each other readily. In bioanalytics, very often labeled, single stranded probes are used in order to find complementary target sequences. If such sequences exist in the sample, the probes will hybridize to said sequences which can then be detected due to the label. Other hybridization based methods comprise microarray and/or biochip methods. Therein, probes are immobilized on a solid phase, which is then exposed to a sample. If complementary nucleic acids exist in the sample, these will hybridize to the probes and can thus be detected. These approaches are also known as "array based methods". Yet another hybridization based method is PCR, which is described below. When it comes to the determination of expression levels, hybridization based methods may for example be used to determine the amount of mRNA for a given gene.

An oligonucleotide capable of specifically binding sequences a gene or fragments thereof relates to an oligonucleotide which specifically hybridizes to a gene or gene product, such as the gene's mRNA or cDNA or to a fragment thereof. To specifically detect the gene or gene product, it is not necessary to detect the entire gene sequence. A fragment of about 20-150 bases will contain enough sequence specific information to allow specific hybridization.

The term "a PCR based method" as used herein refers to methods comprising a polymerase chain reaction (PCR). This is a method of exponentially amplifying nucleic acids, e.g. DNA by enzymatic replication in vitro. As PCR is an in vitro technique, it can be performed without restrictions on the form of DNA, and it can be extensively modified to perform a wide array of genetic manipulations. When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR).

Moreover, PCR-based methods comprise e.g. real time PCR, and, particularly suited for the analysis of expression levels, kinetic or quantitative PCR (qPCR).

The term "Quantitative PCR" (qPCR)" refers to any type of a PCR method which allows the quantification of the template in a sample. Quantitative real-time PCR comprise different techniques of performance or product detection as for example the TaqMan technique or the LightCycler technique. The TaqMan technique, for examples, uses a dual-labelled fluorogenic probe. The TaqMan real-time PCR measures accumulation of a product via the fluorophore during the exponential stages of the PCR, rather than at the end point as in conventional PCR. The exponential increase of the product is used to determine the threshold cycle, CT, i.e. the number of PCR cycles at which a significant exponential increase in fluorescence is detected, and which is directly correlated with the number of copies of DNA template present in the reaction. The set up of the reaction is very similar to a conventional PCR, but is carried out in a real-time thermal cycler that allows measurement of fluorescent molecules in the PCR tubes. Different from regular PCR, in TaqMan real-time PCR a probe is added to the reaction, i.e., a single-stranded oligonucleotide complementary to a segment of 20-60 nucleotides within the DNA template and located between the two primers. A fluorescent reporter or fluorophore (e.g., 6-carboxyfluorescein, acronym: FAM, or tetrachlorofluorescin, acronym: TET) and quencher (e.g., tetramethylrhodamine, acronym: TAMRA, of dihydrocyclopyrroloindole tripeptide 'black hole quencher', acronym: BHQ) are covalently attached to the 5' and 3' ends of the probe, respectively[2]. The close proximity between fluorophore and quencher attached to the probe inhibits fluorescence from the fluorophore. During PCR, as DNA synthesis commences, the 5' to 3' exonuclease activity of the Taq polymerase degrades that proportion of the probe that has annealed to the template. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

By "array" or "matrix" an arrangement of addressable locations or "addresses" on a device is meant. The locations can be arranged in two dimensional arrays, three dimensional arrays, or other matrix formats. The number of locations can range from several to at least hundreds of thousands. Most importantly, each location represents a totally independent reaction site. Arrays include but are not limited to nucleic acid arrays, protein arrays and antibody arrays. A "nucleic acid array" refers to an array containing nucleic acid probes, such as oligonucleotides, nucleotide analogues, polynucleotides, polymers of nucleotide analogues, morpholinos or larger portions of genes. The nucleic acid and/or analogue on the array is preferably single stranded. Arrays wherein the probes are oligonucleotides are referred to as "oligo¬nucleotide arrays" or "oligonucleotide chips." A "microarray," herein also refers to a "biochip" or "biological chip", an array of regions having a density of discrete regions of at least about 100/cm2, and preferably at least about 1000/cm2.

"Primer pairs" and "probes", within the meaning of the invention, shall have the ordinary meaning of this term which is well known to the person skilled in the art of molecular biology. In a preferred embodiment of the invention "primer pairs" and "probes", shall be understood as being polynucleotide molecules having a sequence identical, complementary, homologous, or homologous to the complement of regions of a target polynucleotide which is to be detected or quantified. In yet another embodiment, nucleotide analogues are also comprised for usage as primers and/or probes. Probe technologies used for kinetic or real time PCR applications could be e.g. TaqMan® systems obtainable at Applied Biosystems, extension probes such as Scorpion® Primers, Dual Hybridisation Probes, Amplifluor® obtainable at Chemicon International, Inc, or Minor Groove Binders.

"Individually labeled probes", within the meaning of the invention, shall be understood as being molecular probes comprising a polynucleotide, oligonucleotide or nucleotide analogue and a label, helpful in the detection or quantification of the probe. Preferred labels are fluorescent molecules, luminescent molecules, radioactive molecules, enzymatic molecules and/or quenching molecules.

"Arrayed probes", within the meaning of the invention, shall be understood as being a collection of immobilized probes, preferably in an orderly arrangement. In a preferred embodiment of the invention, the individual "arrayed probes" can be identified by their respective position on the solid support, e.g., on a "chip".

When used in reference to a single-stranded nucleic acid sequence, the term "substantially homologous" refers to any probe that can hybridize (i.e., it is the complement of) the single-stranded nucleic acid sequence under conditions of low stringency as described above.

SUMMARY OF THE INVENTION

In general terms, the present invention provides a method to assess the risk of recurrence of a node negative or positive, estrogen receptor positive and HER2/NEU negative breast cancer patient, in particular patients receiving endocrine therapy, for example when treated with tamoxifen. Estrogen receptor status is generally determined using immunohistochemistry, HER2/NEU (ERBB2) status is generally determined using immunohistochemistry and fluorescence in situ hybridization. However, estrogen receptor status and HER2/NEU (ERBB2) status may, for the purposes of the invention, be determined by any suitable method, e.g. immunohistochemistry, fluorescence in situ hybridization (FISH), or RNA expression analysis.

The present invention relates to a method for predicting an outcome of breast cancer in an estrogen receptor positive and HER2 negative tumor of a breast cancer patient, said method comprising:
(a) determining in a tumor sample from said patient the RNA expression levels of at least 2 of the following 9 genes: UBE2C, BIRC5, RACGAP1, DHCR7, STC2, AZGP1, RBBP8, IL6ST, and MGP
(b) mathematically combining expression level values for the genes of the said set which values were determined in the tumor sample to yield a combined score, wherein said combined score is indicative of a prognosis of said patient. In one embodiment at least 3, 4, 5 or 6 genes are selected.

In a further embodiment of the invention the method comprises:
(a) determining in a tumor sample from said patient the RNA expression levels of the following 8 genes: UBE2C, RACGAP1, DHCR7, STC2, AZGP1, RBBP8, IL6ST, and MGP
(b) mathematically combining expression level values for the genes of the said set which values were determined in the tumor sample to yield a combined score, wherein said combined score is indicative of a prognosis of said patient.

In a further embodiment the method of the invention comprises:
(a) determining in a tumor sample from said patient the RNA expression levels of the following 8 genes: UBE2C, BIRC5, DHCR7, STC2, AZGP1, RBBP8, IL6ST, and MGP;
(b) mathematically combining expression level values for the genes of the said set which values were determined in the tumor sample to yield a combined score, wherein said combined score is indicative of a prognosis of said patient.

In yet another embodiment of the invention

BIRC5 may be replaced by UBE2C or TOP2A or RACGAP1 or AURKA or NEK2 or E2F8 or PCNA or CYBRD1 or DCN or ADRA2A or SQLE or CXCL12 or EPHX2 or ASPH or PRSS16 or EGFR or CCND1 or TRIM29 or DHCR7 or PIP or TFAP2B or WNT5A or APOD or PTPRT with the proviso that after a replacement 8 different genes are selected; and UBE2C may be replaced by BIRC5 or RACGAP1 or TOP2A or AURKA or NEK2 or E2F8 or PCNA or CYBRD1 or ADRA2A or DCN or SQLE or CCND1 or ASPH or CXCL12 or PIP or PRSS16 or EGFR or DHCR7 or EPHX2 or TRIM29 with the proviso that after a replacement 8 different genes are selected; and DHCR7 may be replaced by AURKA, BIRC5, UBE2C or by any other gene that may replace BIRC5 or UBE2C with the proviso that after a replacement 8 different genes are selected; and STC2 may be replaced by INPP4B or IL6ST or SEC14L2 or MAPT or CHPT1 or ABAT or SCUBE2 or ESR1 or RBBP8 or PGR or PTPRT or HSPA2 or PTGER3 with the proviso that after a replacement 8 different genes are selected; and AZGP1 may be replaced by PIP or EPHX2 or PLAT or SEC14L2 or SCUBE2 or PGR with the proviso that after a replacement 8 different genes are selected; and RBBP8 may be replaced by CELSR2 or PGR or STC2 or ABAT or IL6ST with the proviso that after a replacement 8 different genes are selected; and IL6ST may be replaced by INPP4B or STC2 or MAPT or SCUBE2 or ABAT or PGR or SEC14L2 or ESR1 or GJA1 or MGP or EPHX2 or RBBP8 or PTPRT or PLAT with the proviso that after a replacement 8 different genes are selected; and MGP may be replaced by APOD or IL6ST or EGFR with the proviso that after a replacement 8 different genes are selected.

According to an aspect of the invention there is provided a method as described above, wherein said combined score is indicative of benefit from cytotoxic chemotherapy.

Using the method of the invention before a patient receives endocrine therapy allows a prediction of the efficacy of endocrine therapy.

Table 2 below shows whether the overexpression of each of the above marker genes is indicative of a good outcome or a bad outcome in a patient receiving endocrine therapy. The skilled person can thus construct a mathematical combination i.e. an algorithm taking into account the effect of a given genes. For example a summation or weighted summation of genes whose overexpression is indicative of a good outcome results in an algorithm wherein a high risk score is indicative of a good outcome. The validity of the algorithm may be examined by analyzing tumor samples of patients with a clinical record, wherein e.g. the score for good outcome patients and bad outcome patients may be determined separately and compared. The skilled person, a biostatistician, will know to apply further mathematical methods, such as discriminate functions to obtain optimized algorithms. Algorithms may be optimized e.g. for sensitivity or specificity. Algorithms may be adapted to the particular analytical platform used to measure gene expression of marker genes, such as quantitiative PCR.

According to an aspect of the invention there is provided a method as described above, wherein said endocrine therapy comprises tamoxifen or an aromatase inhibitor.

According to an aspect of the invention there is provided a method as described above, wherein a risk of developing recurrence is predicted.

According to an aspect of the invention there is provided a method as described above, wherein said expression level is determined as a non-protein expression level.

According to an aspect of the invention there is provided a method as described above, wherein said expression level is determined as an RNA expression level.

According to an aspect of the invention there is provided a method as described above, wherein said expression level is determined by at least one of
a PCR based method,
a micorarray based method, and
a hybridization based method.

According to an aspect of the invention there is provided a method as described above, wherein said determination of expression levels is in a formalin-fixed paraffin embedded tumor sample or in a fresh-frozen tumor sample.

According to an aspect of the invention there is provided a method as described above, wherein the expression level of said at least on marker gene is determined as a pattern of expression relative to at least one reference gene or to a computed average expression value.

According to an aspect of the invention there is provided a method as described above, wherein said step of mathematically combining comprises a step of applying an algorithm to values representative of an expression level of a given gene.

According to an aspect of the invention there is provided a method as described above, wherein said algorithm is a linear combination of said values representative of an expression level of a given gene.

According to an aspect of the invention there is provided a method as described above, wherein a value for a representative of an expression level of a given gene is multiplied with a coefficient.

According to an aspect of the invention there is provided a method as described above, wherein one, two or more thresholds are determined for said combined score and discriminated into high and low risk, high, intermediate and low risk, or more risk groups by applying the threshold on the combined score.

According to an aspect of the invention there is provided a method as described above, wherein a high combined score is indicative of benefit from a more aggressive therapy, e.g. cytotoxic chemotherapy. The skilled person understands that a "high score" in this regard relates to a reference value or cutoff value. The skilled person further understands that depending on the particular algorithm used to obtain the combined score, also a "low" score below a cut off or reference value can be indicative of benefit from a more aggressive therapy, e.g. cytotoxic chemotherapy. This is the case when genes having a positive correlation with high risk of metastasis factor into the algorithm with a positive coefficient, such that an overall high score indicates high expression of genes having a positive correlation with high risk.

According to an aspect of the invention there is provided a method as described above, wherein an information regarding nodal status of the patient is processed in the step of mathematically combining expression level values for the genes to yield a combined score.

According to an aspect of the invention there is provided a method as described above, wherein said information regarding nodal status is a numerical value ≤0 if said nodal status is negative and said information is a numerical value >0 if said nodal status positive or unknown. In exemplary embodiments of the invention a negative nodal status is assigned the value 0, an unknown nodal status is assigned the value 0.5 and a positive nodal status is assigned the value 1. Other values may be chosen to reflect a different weighting of the nodal status within an algorithm.

The invention further relates to a kit for performing a method as described above, said kit comprising a set of oligonucleotides capable of specifically binding sequences or to sequences of fragments of the genes in a combination of genes, wherein
(i) said combination comprises at least the 8 genes UBE2C, BIRC5, DHCR7, STC2, AZGP1, RBBP8, IL6ST, and MGP; or
(ii) said combination comprises at least the 10 genes BIRC5, AURKA, PVALB, NMU, STC2, RBBP8, PTGER3, CXCL12, CDH1, and PIP; or
(iii) said combination comprises at least the 9 genes BIRC5, DHCR7, RACGAP1, PVALB, STC2, IL6ST, PTGER3, CXCL12, and ABAT; or
(iv) said combination comprises at least the 9 genes DHCR7, RACGAP1, NMU, AZGP1, RBBP8, IL6ST, and MGP;

The invention further relates to the use of a kit for performing a method of any of claims 1 to 17, said kit comprising a set of oligonucleotides capable of specifically binding sequences or to sequences of fragments of the genes in a combination of genes, wherein
(i) said combination comprises at least the 8 genes UBE2C, BIRC5, DHCR7, STC2, AZGP1, RBBP8, IL6ST, and MGP; or
(ii) said combination comprises at least the 10 genes BIRC5, AURKA, PVALB, NMU, STC2, RBBP8, PTGER3, CXCL12, CDH1, and PIP; or
(iii) said combination comprises at least the 9 genes BIRC5, DHCR7, RACGAP1, PVALB, STC2, IL6ST, PTGER3, CXCL12, and ABAT; or
(iv) said combination comprises at least the 9 genes DHCR7, RACGAP1, NMU, AZGP1, RBBP8, IL6ST, and MGP;19. A computer program product capable of processing values representative of an expression level of the genes AKR1C3, MAP4 and SPP1 by mathematically combining said values to yield a combined score, wherein said combined score is indicative of benefit from cytotoxic chemotherapy of said patient.

The invention further relates to a computer program product capable of processing values representative of an expression level of a combination of genes mathematically combining said values to yield a combined score, wherein said combined score is indicative of efficacy or benefit from endocrine therapy of said patient, according to the above methods.

Said computer program product may be stored on a data carrier or implemented on a diagnostic system capable of outputting values representative of an expression level of a given gene, such as a real time PCR system.

If the computer program product is stored on a data carrier or running on a computer, operating personal can input the expression values obtained for the expression level of the respective genes. The computer program product can then apply an algorithm to produce a combined score indicative of benefit from cytotoxic chemotherapy for a given patient.

The methods of the present invention have the advantage of providing a reliable prediction of an outcome of disease based on the use of only a small number of genes. The methods of the present invention have been found to be especially suited for analyzing the response to endocrine treatment, e.g. by tamoxifen, of patients with tumors classified as ESR1 positive and ERBB2 negative.

DETAILED DESCRIPTION OF THE INVENTION

Figure 1:
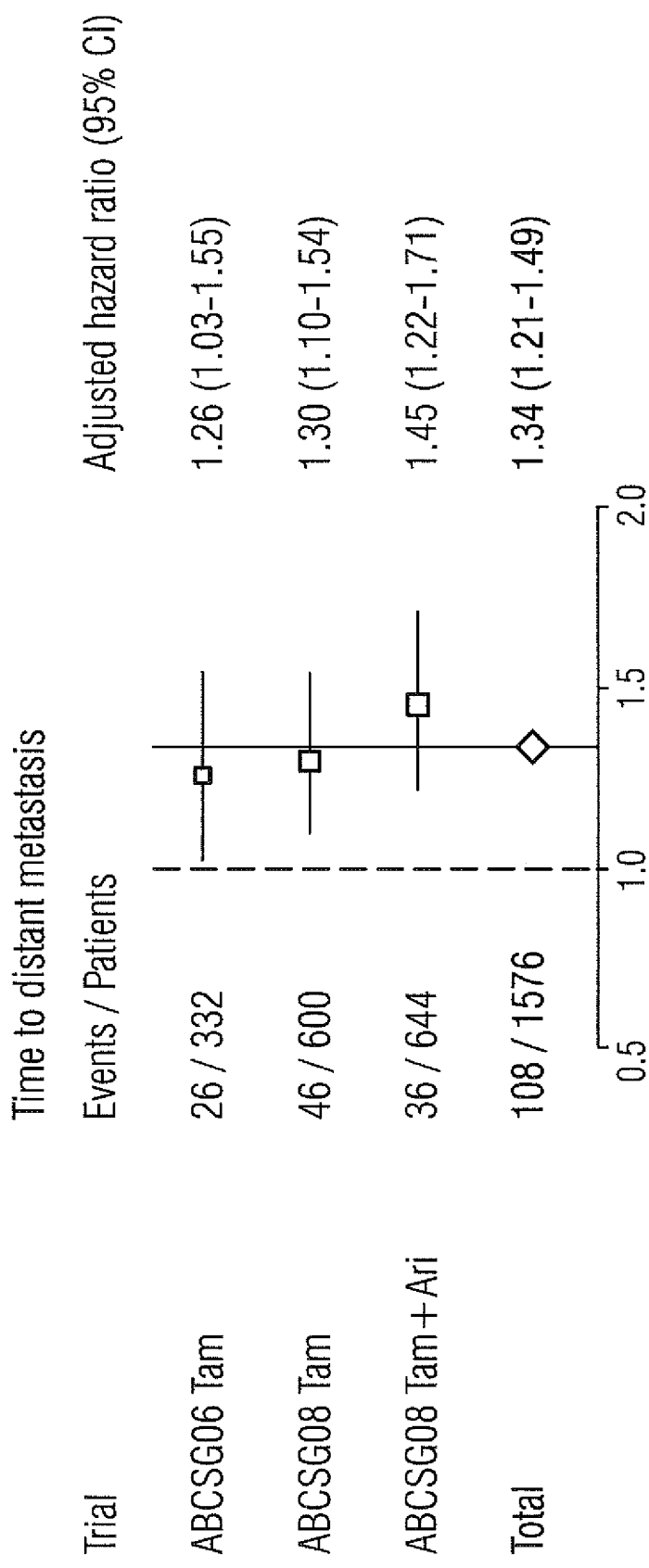
FIG. 1 shows a Forrest Plot of the adjusted hazard unit ratio with 95% confidence interval of the T5 score in the combined cohort, as well as the individual treatment arms of the ABCSG06 and 08 studies, using distant metastasis as endpoint.

The invention is explained in conjunction with exemplary embodiments and the attached figures:

Herein disclosed are unique combinations of marker genes which can be combined into an algorithm for the here presented new predictive test.

Technically, the method of the invention can be practiced using two technologies: 1.) Isolation of total RNA from fresh or fixed tumor tissue and 2.) Kinetic RT-PCR of the isolated nucleic acids. Alternatively, it is contemplated to measure expression levels using alternative technologies, e.g by microarray or by measurement at a protein level.

The methods of the invention are based on quantitative determination of RNA species isolated from the tumor in order to obtain expression values and subsequent bioinformatic analysis of said determined expression values. RNA species might be isolated from any type of tumor sample, e.g. biopsy samples, smear samples, resected tumor material, fresh frozen tumor tissue or from paraffin embedded and formalin fixed tumor tissue. First, RNA levels of genes coding for specific combinations of the genes UBE2C, BIRC5, DHCR7, RACGAP1, AURKA, PVALB, NMU, STC2, AZGP1, RBBP8, IL6ST, MGP, PTGER3, CXCL12, ABAT, CDH1, and PIP or specific combinations thereof, as indicated, are determined. Based on these expression values a prognostic score is calculated by a mathematical combination, e.g. according to formulas T5 T1, T4, or T5b (see below). A high score value indicates a high risk for development of distant metastasis, a low score value indicates a low risk of distant metastasis. Consequently, a high score also indicates that the patient is a high risk patient who will benefit from a more aggressive therapy, e.g. cytotoxic chemotherapy.

The present examples are based on identification of prognostic genes using tumors of patients homogeneously treated in the adjuvant setting with tamoxifen. Furthermore, identification of relevant genes has been restricted to tumors classified as ESR1 positive and ERBB2 negative based on RNA expression levels. In addition, genes allowing separation of intermediate risk, e.g. grade 2 tumors were considered for algorithm development. Finally, a platform transfer from Affymetrix HG_U133a arrays to quantitative real time PCR, as well as a sample type transfer from fresh frozen tissue to FFPE tissue was performed to ensure robust algorithm performance, independent from platform and tissue type. As a result, determination of the expression level of RNA species from the primary tumor and the subsequent complex and multivariate analysis as described above provides a superior method for prediction of the likelihood of disease recurrence in patients diagnosed with lymph node negative or positive early breast cancer, when treated with tamoxifen only in the adjuvant setting. Thus the test relies on fewer genes than those of the competitors but provides superior information regarding high sensitivity and negative predictive value, in particular for tumors considered to exhibit an intermediate risk of recurrence based on standard clinical factors.

The total RNA was extracted with a Siemens, silica bead-based and fully automated isolation method for RNA from one 10 µm whole FFPE tissue section on a Hamilton MICROLAB STARlet liquid handling robot (17). The robot, buffers and chemicals were part of a Siemens VERSANT® kPCR Molecular System (Siemens Healthcare Diagnostics, Tarrytown, N.Y.; not commercially available in the USA). Briefly, 150 µl FFPE buffer (Buffer FFPE, research reagent, Siemens Healthcare Diagnostics) were added to each section and incubated for 30 minutes at 80° C. with shaking to melt the paraffin. After cooling down, proteinase K was added and incubated for 30 minutes at 65° C. After lysis, residual tissue debris was removed from the lysis fluid by a 15 minutes incubation step at 65° C. with 40 µl silica-coated iron oxide beads. The beads with surface-bound tissue debris were separated with a magnet and the lysates were transferred to a standard 2 ml deep well-plate (96 wells). There, the total RNA and DNA was bound to 40 µl unused beads and incubated at room temperature. Chaotropic conditions were produced by the addition of 600 µl lysis buffer. Then, the beads were magnetically separated and the supernatants were discarded. Afterwards, the surface-bound nucleic acids were washed three times followed by magnetization, aspiration and disposal of supernatants. Afterwards, the nucleic acids were eluted by incubation of the beads with 100 µl elution buffer for 10 minutes at 70° C. with shaking. Finally, the beads were separated and the supernatant incubated with 12 µl DNase I Mix (2 µL DNase I (RNase free); 10 µl 10× DNase I buffer; Ambion/Applied Biosystems, Darmstadt, Germany) to remove contaminating DNA. After incubation for 30 minutes at 37° C., the DNA-free total RNA solution was aliquoted and stored at −80° C. or directly used for mRNA expression analysis by reverse transcription kinetic PCR (RTkPCR). All the samples were analyzed with one-step RT-kPCR for the gene expression of up to three reference genes, (RPL37A, CALM2, OAZ1) and up to 16 target genes in an ABI PRISM® 7900HT (Applied Biosystems, Darmstadt, Germany). The SuperScript® III Platinum® One-Step Quantitative RT-PCR System with ROX (6-carboxy-X-rhodamine) (Invitrogen, Karlsruhe, Germany) was used according to the manufacturer's instructions. Respective probes and primers are shown in table 1. The PCR conditions were as follows: 30 minutes at 50° C., 2 minutes at 95° C. followed by 40 cycles of 15 seconds at 95° C. and 30 seconds at 60° C. All the PCR assays were performed in triplicate. As surrogate marker for RNA yield, the housekeeper gene, RPL37A cycle threshold (Ct) value was used as described elsewhere (17). The relative gene expression levels of the target genes were calculated by the delta-Ct method using the formula:

$$20-(Ct(target)-mean(Ct(reference\ genes))).$$

A platform transfer from Affymetrix HG_U133a arrays (fresh frozen tissue) to quantitative real time PCR (FFPE tissue) was calculated as follows. Material from 158 patients was measured using both platforms to yield paired samples. Delta-Ct values were calculated from the PCR data. Log 2-Expressions were calculated from the Affymetrix data by applying a lower bound (setting all values below the lower bound to the lower bound) and then calculating the logarithm of base 2. The application of a lower bound reduces the effect of increased relative measurement noise for low expressed genes/samples; a lower bound of 20 was used, lower bounds between 0.1 and 200 also work well. A HG_U133a probe set was selected for each PCR-measured gene by maximizing the Pearson correlation coefficient between the delta-Ct value (from PCR) and the log 2-expression (from Affymetrix). Other correlation measures will also work well, e.g. the Spearman correlation coefficient. In most cases the best-correlating probe set belonged to the intended gene, for the remaining cases the PCR-gene was removed for further processing. Those genes showing a bad correlation between platforms were also removed, where a threshold on the Pearson correlation coefficient of 0.7 was used (values of between 0.5 and 0.8) also work well. The platform transformation was finalized by calculating unsupervised z-transformations for both platforms and combining them; a single PCR-delta-Ct value then is transformed to the Affymetrix scale by the following steps: (i) apply affine linear transformation where coefficients were determined by z-transformation of PCR data, (ii) apply inverse affine linear transformation where coefficients were determined by z-transformation of Affymetrix data, (iii) invert log 2, i.e. calculate exponential with respect to base 2. Alternatives to the two-fold z-transformations are linear or higher order regression, robust regression or principal component based methods, which will also work well.

The sequences of the primers and probes were as follows:

TABLE 1

Primer and probe sequences for the respective genes:

| gene | probe | Seq ID | forward primer | Seq ID | reverse primer | Seq ID |
|---|---|---|---|---|---|---|
| ABAT | TCGCCCTAAGAGGCTCTTCCTC | 1 | GGCAACTTGAGGTCTGACTTTTG | 2 | GGTCAGCTCACAAGTGGTGTGA | 3 |
| ADRA2A | TTGTCCTTTCCCCCCTCCGTGC | 4 | CCCCAAGAGCTGTTAGGTATCA | 5 | TCAATGACATGATCTCAACCAGAA | 6 |
| APOD | CATCAGCTCTCAACTCCTGGTTTAACA | 7 | ACTCACTAATGGAAAACGGAAAGATC | 8 | TCACCTTCGATTTGATTCACAGTT | 9 |

TABLE 1-continued

Primer and probe sequences for the respective genes:

| gene | probe | Seq ID | forward primer | Seq ID | reverse primer | Seq ID |
|---|---|---|---|---|---|---|
| ASPH | TGGGAGGAAGGCAAGGTGCTCATC | 10 | TGTGCCAACGAGACCAAGAC | 11 | TCGTGCTCAAAGGAGTCATCA | 12 |
| AURKA | CCGTCAGCCTGTGCTAGGCAT | 13 | AATCTGGAGGCAAGGTTCGA | 14 | TCTGGATTTGCCTCCTGTGAA | 15 |
| BIRC5 | AGCCAGATGACGACCCCATAGAGGAACA | 16 | CCCAGTGTTTCTTCTGCTTCAAG | 17 | CAACCGGACGAATGCTTTTT | 18 |
| CELSR2 | ACTGACTTTCCTTCTGGAGCAGGTGGC | 19 | TCCAAGCATGTATTCCAGACTTGT | 20 | TGCCCACAGCCTCTTTTTCT | 21 |
| CHPT1 | CCACGGCCACCGAAGAGGCAC | 22 | CGCTCGTGCTCATCTCCTACT | 23 | CCCAGTGCACATAAAAGGTATGTC | 24 |
| CXCL12 | CCACAGCAGGGTTTCAGGTTCC | 25 | GCCACTACCCCCTCCTGAA | 26 | TCACCTTGCCAACAGTTCTGAT | 27 |
| CYBRD1 | AGGGCATCGCCATCATCGTC | 28 | GTCACCGGCTTCGTCTTCA | 29 | CAGGTCCACGGCAGTCTGT | 30 |
| DCN | TCTTTTCAGCAACCCGGTCCA | 31 | AAGGCTTCTTATTCGGGTGTGA | 32 | TGGATGGCTGTATCTCCCAGTA | 33 |
| DHCR7 | TGAGCGCCCACCCTCTCGA | 34 | GGGCTCTGCTTCCCGATT | 35 | AGTCATAGGGCAAGCAGAAAATTC | 36 |
| E2F8 | CAGGATACCTAATCCCTCTCACGCAG | 37 | AAATGTCTCCGCAACCTTGTTC | 38 | CTGCCCCCAGGGATGAG | 39 |
| EPHX2 | TGAAGCGGGAGGACTTTTTGTAAA | 40 | CGATGAGAGTGTTTTATCCATGCA | 41 | GCTGAGGCTGGGCTCTTCT | 42 |
| ESR1 | ATGCCCTTTTGCCGATGCA | 43 | GCCAAATTGTGTTTGATGGATTAA | 44 | GACAAAACCGAGTCACATCAGTAATAG | 45 |
| GJA1 | TGCACAGCCTTTTGATTTCCCCGAT | 46 | CGGGAAGCACCATCTCTAACTC | 47 | TTCATGTCCAGCAGCTAGTTTTTT | 48 |
| HSPA2 | CAAGTCAGCAAACACGCAAAA | 49 | CATGCACGAACTAATCAAAAATGC | 50 | ACATTATTCGAGGTTTCTCTTTAATGC | 51 |
| IL6ST | CAAGCTCCACCTTCCAAAGGACCT | 52 | CCCTGAATCCATAAAGGCATACC | 53 | CAGCTTCGTTTTTCCCTACTTTTT | 54 |
| INPP4B | TCCGAGCGCTGGATTGCATGAG | 55 | GCACCAGTTACACAAGGACTTCTTT | 56 | TCTCTATGCGGCATCCTTCTC | 57 |
| MAPT | AGACTATTTGCACACTGCCGCCT | 58 | GTGGCTCAAAGGATAATATCAAACAC | 59 | ACCTTGCTCAGGTCAACTGGTT | 60 |
| MGP | CCTTCATATCCCTCAGCAGAGATGG | 61 | CCTTCATTAACAGGAGAAATGCAA | 62 | ATTGAGCTCGTGGACAGGCTTA | 63 |
| NEK2 | TCCTGAACAAATGAATCGCATGTCCTACAA | 64 | ATTTGTTGGCACACCTTATTACATGT | 65 | AAGCAGCCCAATGACCAGATa | 66 |
| PCNA | AAATACTAAAATGCGCCGGCAATGA | 67 | GGGCGTGAACCTCACCAGTA | 68 | CTTCGGCCCTTAGTGTAATGATATC | 69 |

TABLE 1-continued

Primer and probe sequences for the respective genes:

| gene | probe | Seq ID | forward primer | Seq ID | reverse primer | Seq ID |
|---|---|---|---|---|---|---|
| PGR | TTGATAGAAACGCTGTGAGCTCGA | 70 | AGCTCATCAAGGCAATTGGTTT | 71 | ACAAGATCATGCAAGTTATCAAGAAGTT | 72 |
| PIP | TGCATGGTGGTTAAAACTTACCTCA | 73 | TGCTTGCAGTTCAAACAGAATTG | 74 | CACCTTGTAGAGGGATGCTGCTA | 75 |
| PLAT | CAGAAAGTGGCCATGCCACCCTG | 76 | TGGGAAGACATGAATGCACACTA | 77 | GGAGGTTGGGCTTTAGCTGAA | 78 |
| PRSS16 | CACTGCCGGTCACCCACACCA | 79 | CTGAGGAGCACAGAACCTCAACT | 80 | CGAACTCGGTACATGTCTGATACAA | 81 |
| PTGER3 | TCGGTCTGCTGGTCTCCGCTCC | 82 | CTGATTGAAGATCATTTTCAACATCA | 83 | GACGGCCATTCAGCTTATGG | 84 |
| PTPRT | TTGGCTTCTGGACACCCTCACA | 85 | GAGTTGTGGCCTCTACCATTGC | 86 | GAGCGGGAACCTTGGGATAG | 87 |
| RACGAP1 | ACTGAGAATCTCCACCCGGCGCA | 88 | TCGCCAACTGGATAAATTGGA | 89 | GAATGTGCGGAATCTGTTTGAG | 90 |
| RBBP8 | ACCGATTCCGCTACATTCCACCCAAC | 91 | AGAAATTGGCTTCCTGCTCAAG | 92 | AAAACCAACTTCCCAAAAATTCTCT | 93 |
| SCUBE2 | CTAGAGGGTTCCAGGTCCCATACGTGACATA | 94 | TGTGGATTCAGTTCAAGTCCAATG | 95 | CCATCTCGAACTATGTCTTCAATGAGT | 96 |
| SEC14L2 | TGGGAGGCATGCAACGCGTG | 97 | AGGTCTTACTAAGCAGTCCCATCTCT | 98 | CGACCGGCACCTGAACTC | 99 |
| SQLE | TATGCGTCTCCCAAAAGAAGAACACCTCG | 100 | GCAAGCTTCCTTCCTCCTTCA | 101 | CCTTTAGCAGTTTTCTCCATAGTTTTATATC | 102 |
| TFAP2B | CAACACCACCACTAACAGGCACACGTC | 103 | GGCATGGACAAGATGTTCTTGA | 104 | CCTCCTTGTCGCCAGTTTTACT | 105 |
| TOP2A | CAGATCAGGACCAAGATGGTTCCCACAT | 106 | CATTGAAGACGCTTCGTTATGG | 107 | CCAGTTGTGATGGATAAAATTAATCAG | 108 |
| TRIM29 | TGCTGTCTCACTACCGGCCATTCTACG | 109 | TGGAAATCTGGCAAGCAGACT | 110 | CAATCCCGTTGCCTTTGTTG | 111 |
| UBE2C | TGAACACACATGCTGCCGAGCTCTG | 112 | CTTCTAGGAGAACCCAACATTGATAGT | 113 | GTTTCTTGCAGGTACTTCTTAAAAGCT | 114 |
| WNT5A | TATTCACATCCCCTCAGTTGCAGTGAATTG | 115 | CTGTGGCTCTTAATTTATTGCATAATG | 116 | TTAGTGCTTTTTGCTTTCAAGATCTT | 117 |
| STC2 | TCTCACCTTGACCCTCAGCCAAG | 118 | ACATTTGACAAATTTCCCTTAGGATT | 119 | CCAGGACGCAGCTTTACCAA | 120 |
| AZGP1 | CACCAGCCACCAGGCCCCAG | 121 | TCCTGGACCGGCAAGATC | 122 | TAGGCCAGGCACTTCAGTTTC | 123 |
| CALM2 | TCGCGTCTCGGAAACCGGTAGC | 124 | GAGCGAGCTGAGTGGTTGTG | 125 | AGTCAGTTGGTCAGCCATGCT | 126 |
| CDH1 | CCTGCCAATCCCGATGAAATTGGAAAT | 127 | TGAGTGTCCCCCGGTATCTTC | 128 | TCAGCCGCTTTCAGATTTTCA | 129 |
| NMU | ACCCTGCTGACCTTCTTCCATTCCGT | 130 | AGAAATTGGCTTCCTGCTCAAG | 131 | AAAACCAACTTCCCAAAAATTCTCT | 132 |
| OAZ1 | TGCTTCCACAAGAACCGCGAGGA | 133 | CGAGCCGACCATGTCTTCAT | 134 | AAGCCCAAAAAGCTGAAGGTT | 135 |
| PVALB | AAGTTCTTCCAAATGGTCGGCC | 136 | CCGACTCCTTCGACCACAA | 137 | CATCATCCGCACTCTTTTTCTTC | 138 |
| RPL37A | TGGCTGGCGGTGCCTGGA | 139 | TGTGGTTCCTGCATGAAGACA | 140 | GTGACAGCGGAAGTGGTATTGTAC | 141 |

Table 2, below, lists the genes used in the methods of the invention and in the particular embodiments T5, T1, T4, and T5b. Table 2 also shows whether overexpression of a given gene is indicative of good or bad outcome under Tamoxifen therapy, Table 2 lists the function of the gene, the compartment localization within the cell and the cellular processes it is involved in.

TABLE 2

List of genes of algorithms T5, T1, T4, and T5b:

| Gene | Name | High Expression | Function | Component | Process |
|------|------|-----------------|----------|-----------|---------|
| UBE2C | ubiquitin-conjugating enzyme E2C | Bad Outcome | ATP binding | cytosol | cell division |
| BIRC5 | baculoviral IAP repeat-containing 5 | Bad Outcome | Ran GTPase binding | cytosol | cell cycle |
| DHCR7 | 7-dehydrocholesterol reductase | Bad Outcome | 7-dehydrocholesterol reductase activity | endoplasmatic reticulum membrane | regulation of cell proliferation |
| RACGAP1 | Rac GTPase activating protein 1 | Bad Outcome | GTPase activator activity | cytoplasm | cell cycle |
| AURKA | aurora kinase A | Bad Outcome | ATP binding | centrosome | mitotic cell cycle |
| PVALB | parvalbumin | Bad Outcome | calcium ion binding | | |
| NMU | neuromedin U | Bad Outcome | receptor binding | extracellular region | signal transduction |
| STC2 | stanniocalcin 2 | Good Outcome | hormone activity | extracellular region | cell surface receptor linked signal transduction |
| AZGP1 | alpha-2-glycoprotein 1 | Good Outcome | protein transmembrane transporter activity | extracellular region | negative regulation of cell proliferation |
| RBBP8 | retinoblastoma binding protein 8 | Good Outcome | protein binding | nucleus | cell cycle checkpoint |
| IL6ST | interleukin 6 signal transducer | Good Outcome | receptor activity | extracellular region | signal transduction |
| MGP | matrix Gla protein | Good Outcome | extracellular matrix structural constituent | extracellular region | cell differentiation |
| PTGER3 | prostaglandin E receptor 3 | Good Outcome | ligand-dependent receptor activity | plasma membrane | signal transduction |
| CXCL12 | chemokine (C-XC motif) ligand 12 | Good Outcome | chemokine activity | extracellular region | signal transduction |
| ABAT | 4-aminobutyrate aminotransferase | Good Outcome | transferase activity | mitochondrion | gamma-aminobutyric acid catabolic process |
| CDH1 | cadherin 1 | Good Outcome | cell adhesion molecule binding | plasma membrane | homophilic cell adhesion |
| PIP | prolactin-induced protein | Good Outcome | actin bindin | extracellular region | |
| CALM2 | | | | | Reference Gene |
| OAZ1 | | | | | Reference Gene |
| RPL37A | | | | | Reference Gene |

Table 3, below, shows the combinations of genes used for each algorithm.

TABLE 3

Combination of genes for the respective algorithms:

| Gene | Algo_T1 | Algo_T4 | Algo_T5 | Algo_T5b |
|---|---|---|---|---|
| UBE2C | | | X | |
| BIRC5 | X | X | X | |
| DHCR7 | | X | X | X |
| RACGAP1 | | X | | X |
| AURKA | X | | | |
| PVALB | X | X | | |
| NMU | X | | | X |
| STC2 | X | X | X | |
| AZGP1 | | | X | X |
| RBBP8 | X | | X | X |
| IL6ST | | X | X | X |
| MGP | | | X | X |
| PTGER3 | X | X | | |
| CXCL12 | X | X | | |
| ABAT | | X | | |
| CDH1 | X | | | |
| PIP | X | | | |

Table 4, below, shows Affy probeset ID and TaqMan design ID mapping of the marker genes of the present invention.

TABLE 4

Gene symbol, Affy probeset ID and TaqMan design ID mapping:

| Gene | Design ID | Probeset ID |
|---|---|---|
| UBE2C | R65 | 202954_at |
| BIRC5 | SC089 | 202095_s_at |
| DHCR7 | CAGMC334 | 201791_s_at |
| RACGAP1 | R125-2 | 222077_s_at |
| AURKA | CAGMC336 | 204092_s_at |
| PVALB | CAGMC339 | 205336_at |
| NMU | CAGMC331 | 206023_at |
| STC2 | R52 | 203438_at |
| AZGP1 | CAGMC372 | 209309_at |
| RBBP8 | CAGMC347 | 203344_s_at |
| IL6ST | CAGMC312 | 212196_at |
| MGP | CAGMC383 | 202291_s_at |
| PTGER3 | CAGMC315 | 213933_at |
| CXCL12 | CAGMC342 | 209687_at |
| ABAT | CAGMC338 | 209460_at |
| CDH1 | CAGMC335 | 201131_s_at |

Table 5, below, shows full names, Entrez GeneID, gene bank accession number and chromosomal location of the marker genes of the present invention

| Official Symbol | Official Full Name | Entrez GeneID | Accesion Number | Location |
|---|---|---|---|---|
| UBE2C | ubiquitin-conjugating enzyme E2C | 11065 | U73379 | 20q13.12 |
| BIRC5 | baculoviral IAP repeat-containing 5 | 332 | U75285 | 17q25 |
| DHCR7 | 7-dehydrocholesterol reductase | 1717 | AF034544 | 11q13.4 |
| STC2 | staniocalcin 2 | 8614 | AB012664 | 5q35.2 |
| RBBP8 | retinoblastoma binding protein 8 | 5932 | AF043431 | 18q11.2 |
| IL6ST | interleukin 6 signal transducer | 3572 | M57230 | 5q11 |
| MGP | matrix Gla protein | 4256 | M58549 | 12p12.3 |
| AZGP1 | alpha-2-glycoprotein 1, zinc-binding | 563 | BC005306 | 11q22.1 |
| RACGAP1 | Rac GTPase activating protein 1 | 29127 | NM_013277 | 12q13 |
| AURKA | aurora kinase A | 6790 | BC001280 | 20q13 |
| PVALB | parvalbumin | 5816 | NM_002854 | 22q13.1 |
| NMU | neuromedin U | 10874 | X76029 | 4q12 |
| PTGER3 | prostaglandin E receptor 3 (subtype EP3) | 5733 | X83863 | 1p31.2 |
| CXCL12 | chemokine (C-X-C motif) ligand 12 (stromal cell-derived factor 1) | 6387 | L36033 | 10q11.1 |
| ABAT | 4-aminobutyrat aminotransferase | 18 | L32961 | 16p13.2 |
| CDH1 | cadherin 1, type 1, E-cadherin (epithelial) | 999 | L08599 | 16q22.1 |
| PIP | prolactin-induced protein | 5304 | NMM_002652 | 7q32-qter |

Example Algorithm T5:

Algorithm T5 is a committee of four members where each member is a linear combination of two genes. The mathematical formulas for T5 are shown below; the notation is the same as for T1. T5 can be calculated from gene expression data only.

$$\text{riskMember1} = 0.434039\ [0.301\ldots0.567]^* \\ (0.939*BIRC5 -3.831) - 0.491845\ [-0.714\ldots \\ -0.270]^*(0.707*RBBP8 -0.934)$$

$$\text{riskMember2} = 0.488785\ [0.302\ldots0.675]^* \\ (0.794*UBE2C -1.416) - 0.374702\ [-0.570\ldots \\ -0.179]^*(0.814*IL6ST -5.034)$$

$$\text{riskMember3} = -0.39169\ [-0.541\ldots-0.242]^* \\ (0.674*AZGP1 -0.777) + 0.44229\ [0.256\ldots \\ 0.628]^*(0.891*DHCR7 -4.378)$$

$$\text{riskMember4} = -0.377752\ [-0.543\ldots-0.212]^* \\ (0.485*MGP +4.330) - 0.177669\ [-0.267\ldots \\ -0.088]^*(0.826*STC2 -3.630)$$

$$\text{risk} = \text{riskMember1} + \text{riskMember2} + \text{riskMember3} + \text{riskMember4}$$

Coefficients on the left of each line were calculated as COX proportional hazards regression coefficients, the numbers in squared brackets denote 95% confidence bounds for these coefficients. In other words, instead of multiplying the term (0.939*BIRC5 −3.831) with 0.434039, it may be multiplied with any coefficient between 0.301 and 0.567 and still give a predictive result with in the 95% confidence bounds. Terms in round brackets on the right of each line denote a platform transfer from PCR to Affymetrix: The variables PVALB, CDH1, . . . denote PCR-based expressions normalized by the reference genes (delta-Ct values), the whole term within round brackets corresponds to the logarithm (base 2) of Affymetrix microarray expression values of corresponding probe sets.

Performance of the algorithm T5 was tested in Tamoxifen or Anastrozole treated patients with no more than 3 positive lymph nodes and ER+, HER2-tumors, who participated in the randomized clinical trials ABCSG06 (n=332) or ABCSG08 (n=1244). As shown in FIG. 1, Cox regression analysis reveals, that the T5 score has a significant association with the development of distant metastasis in all cohorts tested.

Figure 2:
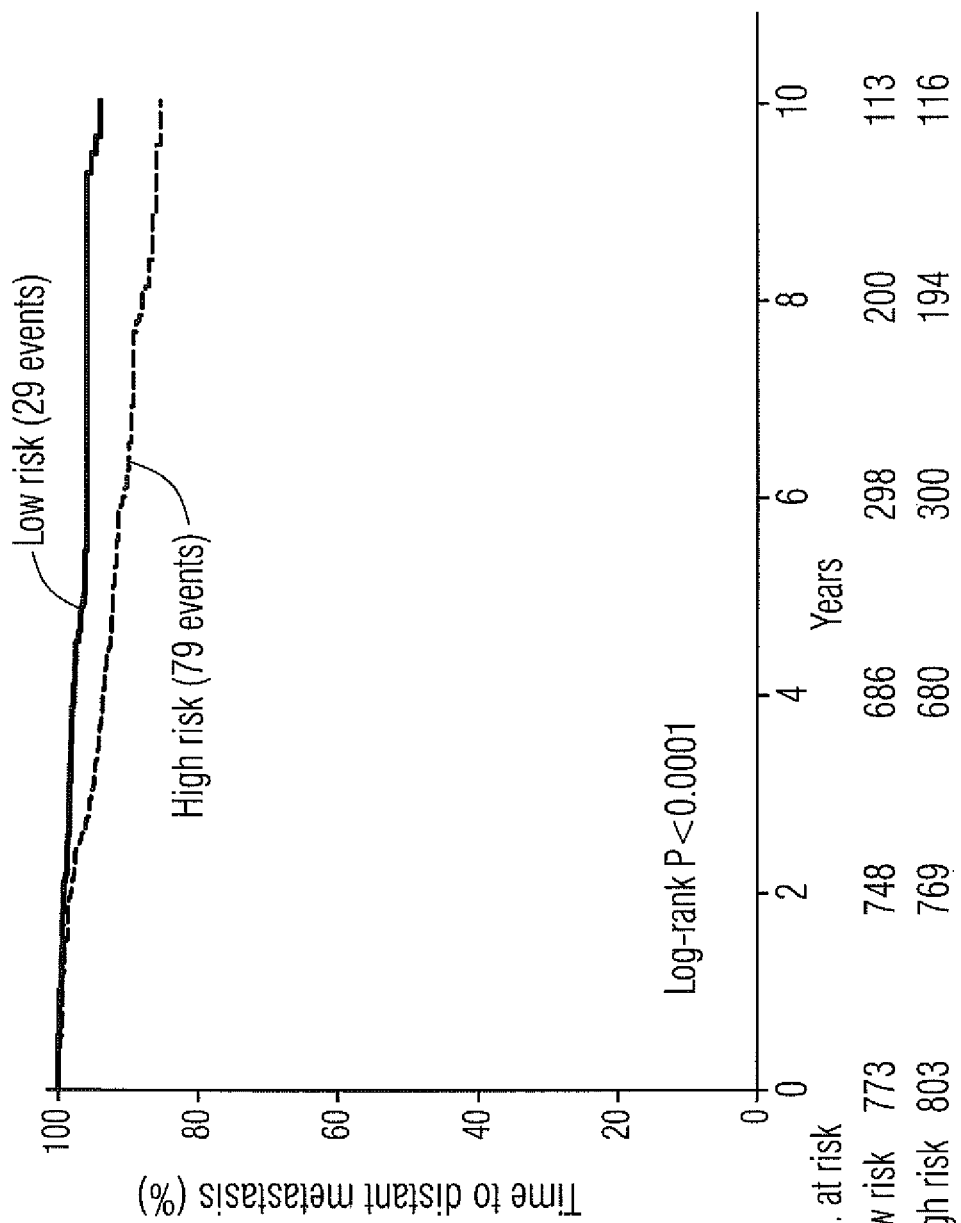
FIG. 2 shows a Kaplan Meier Analysis of ER+, HER−, N0-3 patients from the combined ABCSG06 and 08 cohorts, stratified as high or low risk according to T5 Score value.

Kaplan Meier analysis was performed, after classifying the patients of the combined ABCSG cohorts using a predefined cut off for T5 score. Patients with a low risk of development of a distant metastasis had a T5 score ≤−9.3, while patients with a high risk of development of a distant metastasis had a T5 score above −9.3. As shown in FIG. 2, a highly significant separation of both risk groups is observed.

Importantly, the T5 score was evaluated and compared against "Adjuvant!Online", an online tool to aid in therapy selection based on entry of clinical parameters such as tumor size, tumor grade and nodal status. When the T5 score was tested by bivariate Cox regression against the Adjuvant!Online Relapse Risk score, both scores remained a significant association with the development of distant metastasis. Bivariate Cox regression using dichotomized data, which were stratified according to T5 (cut off −9.3) respectively to Adjuvant!Online (cut off 8), again yielded highly significant and independent associations with time to metastasis as clinical endpoint.

TABLE 6

Bivariate Cox regression von T5 und Adjuvant!Online

| Variable | Hazard ratio | 95% CI* | P |
|---|---|---|---|
| Adjuvant!Online | 2.36 | 1.58-3.54 | <0.0001 |
| Gene-expression signature (risk group) | 2.62 | 1.71-4.01 | <0.0001 |
| Adjuvant!Online (score) | 1.04 | 1.02-1.06 | <0.0001 |
| Gene-expression signature (risk group) | 1.35 | 1.21-1.49 | <0.0001 | with HR = Hazard Ratio, 95% CI = 95% Confidence Interval, p = P value.

Exemplary Kaplan Meyer Curves are shown in FIG. 1 wherein High=High Risk Group, Low=Low Risk Group according to a predefined cut off A high value of the T5 score indicates an increased risk of occurrence of distant metastasis in a given time period.

This has been shown to be the case for patients having been treated with tamoxifen and also for patients having been treated with aromatase inhibitors.

Example Algorithm T1:

Algorithm T1 is a committee of three members where each member is a linear combination of up to four variables. In general variables may be gene expressions or clinical variables. In T1 the only non-gene variable is the nodal status coded 0, if patient is lymph-node negative and 1, if patient is lymph-node-positive. The mathematical formulas for T1 are shown below.

$$riskMember1 = +0.193935\ [0.108\ldots 0.280]*\\(0.792*PVALB\ -2.189) - 0.240252\ [-0.400\ldots\\-0.080]*(0.859*CDH1\ -2.900) - 0.270069\\{}[-0.385\ldots -0.155]*(0.821*STC2\ -3.529)\\+1.2053\ [0.534-1.877]*nodalStatus$$

$$riskMember2 = -0.25051\ [-0.437\ldots -0.064]*\\(0.558*CXCL12\ +0.324) - -0.421992\\{}[-0.687\ldots -0.157]*(0.715*RBBP8\ -1.063)+\\0.148497\ [0.029\ldots 0.268]*(1.823*NMU\\-12.563) + 0.293563\ [0.108\ldots 0.479]*\\(0.989*BIRC5\ -4.536)$$

$$riskMember3 = +0.308391\ [0.074\ldots 0.543]*\\(0.812*AURKA\ -2.656) - 0.225358\ [-0.395\ldots\\-0.055]*(0.637*PTGER3\ +0.492) - 0.116312\\{}[-0.202\ldots -0.031]*(0.724*PIP\ +0.985)$$

$$risk = +riskMember1 + riskMember2 + riskMember3$$

Coefficients on the left of each line were calculated as COX proportional hazards regression coefficients, the numbers in squared brackets denote 95% confidence bounds for these coefficients. Terms in round brackets on the right of each line denote a platform transfer from PCR to Affymetrix: The variables PVALB, CDH1, . . . denote PCR-based expressions normalized by the reference genes, the whole term within round brackets corresponds to the logarithm (base 2) of Affymetrix microarray expression values of corresponding probe sets.

Example Algorithm T4:

Algorithm T4 is a linear combination of motifs. The top 10 genes of several analyses of Affymetrix datasets and PCR data were clustered to motifs. Genes not belonging to a cluster were used as single gene-motifs. COX proportional hazards regression coefficients were found in a multivariate analysis.

In general motifs may be single gene expressions or mean gene expressions of correlated genes. The mathematical formulas for T4 are shown below.

$$prolif = ((0.84\ [0.697\ldots 0.977]*RACGAP1\ -2.174)+\\(0.85\ [0.713\ldots 0.988]*DHCR7\ -3.808)+(0.94\\{}[0.786\ldots 1.089]*BIRC5\ -3.734))/3$$

$$motiv2 = ((0.83\ [0.693\ldots 0.96]*IL6ST\ -5.295)+\\(1.11\ [0.930\ldots 1.288]*ABAT -7.019)+(0.84\\{}[0.701\ldots 0.972]*STC2\ -3.857))/3$$

$$ptger3 = (PTGER3*0.57\ [0.475\ldots 0.659]+1.436)$$

$$cxcl12 = (CXCL12*0.53\ [0.446\ldots 0.618]+0.847)$$

$$pvalb = (PVALB*0.67\ [0.558\ldots 0.774]-0.466)$$

Factors and offsets for each gene denote a platform transfer from PCR to Affymetrix: The variables RACGAP1, DHCR7, . . . denote PCR-based expressions normalized by CALM2 and PPIA, the whole term within round brackets corresponds to the logarithm (base 2) of Affymetrix microarray expression values of corresponding probe sets.

The numbers in squared brackets denote 95% confidence bounds for these factors.

As the algorithm performed even better in combination with a clinical variable the nodal status was added. In T4 the nodal status is coded 0, if patient is lymph-node negative and 1, if patient is lymph-node-positive. With this, algorithm T4 is:

$$risk = -0.32\ [-0.510\ldots -0.137]*motiv2 + 0.65\\{}[0.411\ldots 0.886]*prolif - 0.24\ [-0.398\ldots\\-0.08]*ptger3 - 0.05\ [-0.225\ldots 0.131]*cxcl12+\\0.09\ [0.019\ldots 0.154]*pvalb + nodalStatus$$

Coefficients of the risk were calculated as COX proportional hazards regression coefficients, the numbers in squared brackets denote 95% confidence bounds for these coefficients.

Algorithm T5b is a committee of two members where each member is a linear combination of four genes. The mathematical formulas for T5b are shown below, the notation is the same as for T1 and T5. In T5b a non-gene variable is the nodal status coded 0, if patient is lymph-node negative and 1, if patient is lymph-node-positive and 0.5 if the lymph-node status is unknown. T5b is defined by:

$$riskMember1 = 0.359536\ [0.153\ldots 0.566]*\\(0.891*DHCR7\ -4.378) - 0.288119\ [-0.463\ldots\\-0.113]*(0.485*MGP\ +4.330) + 0.257341\\{}[0.112\ldots 0.403]*(1.118*NMU\ -5.128)-\\0.337663\ [-0.499\ldots -0.176]*(0.674*AZGP1\\-0.777)$$

riskMember2=−0.374940 [−0.611 . . . −0.139]*
(0.707*RBBP8 −0.934)−0.387371 [−0.597 . . .
−0.178]*(0.814*IL6ST −5.034)+0.800745
[0.551 . . . 1.051]*(0.860*RACGAP1 −2.518)+
0.770650 [0.323 . . . 1.219]*Nodalstatus risk=riskMember1+riskMember2

The skilled person understands that these algorithms represent particular examples and that based on the information regarding association of gene expression with outcome as given in table 2 alternative algorithms can be established using routine skills.

Algorithm Simplification by Employing Subsets of Genes

"Example algorithm T5" is a committee predictor consisting of 4 members with 2 genes of interest each. Each member is an independent and self-contained predictor of distant recurrence, each additional member contributes to robustness and predictive power of the algorithm to predict time to metastasis, time to death or likelihood of survival for a breast cancer patient. The equation below shows the "Example Algorithm T5"; for ease of reading the number of digits after the decimal point has been truncated to 2; the range in square brackets lists the estimated range of the coefficients (mean+/−3 standard deviations).

T5 Algorithm:

+0.41 [0.21 . . . 0.61]*BIRC5 −0.33 [−0.57 . . .
−0.09]*RBBP8

+0.38 [0.15 . . . 0.61]*UBE2C −0.30 [−0.55 . . .
−0.06]*IL6ST

−0.28 [−0.43 . . . −0.12]*AZGP1+0.42 [0.16 . . .
0.68]*DHCR7

−0.18 [−0.31 . . . −0.06]*MGP −0.13 [−0.25 . . .
−0.02]*STC2 c-indices: trainSet=0.724,

Gene names in the algorithm denote the difference of the mRNA expression of the gene compared to one or more housekeeping genes as described above.

Analysing a cohort different from the finding cohort (234 tumor samples) it was surprising to learn that some simplifications of the "original T5 Algorithm" still yielded a diagnostic performance not significantly inferior to the original T5 algorithm. The most straightforward simplification was reducing the committee predictor to one member only. Examples for the performance of the "one-member committees" are shown below:

member 1 only:

+0.41 [0.21 . . . 0.61]*BIRC5 −0.33 [−0.57 . . .
−0.09]*RBBP8 c-indices: trainSet=0.653, independentCohort=0.681 member 2 only:

+0.38 [0.15 . . . 0.61]*UBE2C −0.30 [−0.55 . . .
−0.06]*IL6ST c-indices: trainSet=0.664, independentCohort=0.696 member 3 only:

−0.28 [−0.43 . . . −0.12]*AZGP1+0.42 [0.16 . . .
0.68]*DHCR7 c-indices: trainSet=0.666, independentCohort=0.601 member 4 only:

−0.18 [−0.31 . . . −0.06]*MGP −0.13 [−0.25 . . .
−0.02]*STC2 c-indices: trainSet=0.668, independentCohort=0.593

The performance of the one member committees as shown in an independent cohort of 234 samples is notably reduced compared to the performance of the full algorithm. Still, using a committee consisting of fewer members allows for a simpler, less costly estimate of the risk of breast cancer recurrence or breast cancer death that might be acceptable for certain diagnostic purposes.

Gradually combining more than one but less than four members to a new prognostic committee predictor algorithm, frequently leads to a small but significant increase in the diagnostic performance compared to a one-member committee. It was surprising to learn that there were marked improvements by some combination of committee members while other combinations yielded next to no improvement. Initially, the hypothesis was that a combination of members representing similar biological motives as reflected by the employed genes yielded a smaller improvement than combining members reflecting distinctly different biological motives. Still, this was not the case. No rule could be identified to foretell the combination of some genes to generate an algorithm exhibiting more prognostic power than another combination of genes. Promising combinations could only be selected based on experimental data.

Identified combinations of combined committee members to yield simplified yet powerful algorithms are shown below.

members 1 and 2 only:

+0.41 [0.21 . . . 0.61]*BIRC5 −0.33 [−0.57 . . .
−0.09]*RBBP8

+0.38 [0.15 . . . 0.61]*UBE2C −0.30 [−0.55 . . .
−0.06]*IL6ST c-indices: trainSet=0.675, independentCohort=0.712 members 1 and 3 only:

+0.41 [0.21 . . . 0.61]*BIRC5 −0.33 [−0.57 . . .
−0.09]*RBBP8

−0.28 [−0.43 . . . −0.12]*AZGP1+0.42 [0.16 . . .
0.68]*DHCR7 c-indices: trainSet=0.697, independentCohort=0.688 members 1 and 4 only:

+0.41 [0.21 . . . 0.61]*BIRC5 −0.33 [−0.57 . . .
−0.09]*RBBP8

−0.18 [−0.31 . . . −0.06]*MGP −0.13 [−0.25 . . .
−0.02]*STC2 c-indices: trainSet=0.705, independentCohort=0.679 members 2 and 3 only:

+0.38 [0.15 . . . 0.61]*UBE2C −0.30 [−0.55 . . .
−0.06]*IL6ST

−0.28 [−0.43 . . . −0.12]*AZGP1+0.42 [0.16 . . .
0.68]*DHCR7 c-indices: trainSet=0.698, independentCohort=0.670 members 1, 2 and 3 only:

+0.41 [0.21 . . . 0.61]*BIRC5 −0.33 [−0.57 . . .
−0.09]*RBBP8

+0.38 [0.15 ... 0.61]*UBE2C −0.30 [−0.55 ...
−0.06]*IL6ST

−0.28 [−0.43 ... −0.12]*AZGP1+0.42 [0.16 ...
0.68]*DHCR7 c-indices: trainSet=0.701, independentCohort=0.715

Not omitting complete committee members but a single gene or genes from different committee members is also possible but requires a retraining of the entire algorithm. Still, it can also be advantageous to perform. The performance of simplified algorithms generated by omitting entire members or individual genes is largely identical.

Algorithm Variants by Gene Replacement

Described algorithms, such as "Example algorithm T5", above can be also be modified by replacing one or more genes by one or more other genes. The purpose of such modifications is to replace genes difficult to measure on a specific platform by a gene more straightforward to assay on this platform. While such transfer may not necessarily yield an improved performance compared to a starting algorithm, it can yield the clue to implanting the prognostic algorithm to a particular diagnostic platform. In general, replacing one gene by another gene while preserving the diagnostic power of the predictive algorithm can be best accomplished by replacing one gene by a co-expressed gene with a high correlation (shown e.g. by the Pearson correlation coefficient). Still, one has to keep in mind that the mRNA expression of two genes highly correlative on one platform may appear quite independent from each other when assessed on another platform. Accordingly, such an apparently easy replacement when reduced to practice experimentally, may yield disappointingly poor results as well as surprising strong results, always depending on the imponderabilia of the platform employed. By repeating this procedure one can replace several genes.

The efficiency of such an approach can be demonstrated by evaluating the predictive performance of the T5 algorithm score and its variants on the validation cohorts. The following table shows the c-index with respect to endpoint distant recurrence in two validation cohorts.

TABLE 7

| Variant | Validation Study A | Validation Study B |
|---|---|---|
| original algorithm T5 | c-index = 0.718 | c-index = 0.686 |
| omission of BIRC5 (setting expression to some constant) | c-index = 0.672 | c-index = 0.643 |
| replacing BIRC5 by UBE2C (no adjustment of the coefficient) | c-index = 0.707 | c-index = 0.678 |

One can see that omission of one of the T5 genes, here shown for BIRC5 for example, notably reduces the predictive performance. Replacing it with another gene yields about the same performance.

A better method of replacing a gene is to re-train the algorithm. Since T5 consists of four independent committee members one has to re-train only the member that contains the replaced gene. The following equations demonstrate replacements of genes of the T5 algorithm shown above trained in a cohort of 234 breast cancer patients. Only one member is shown below, for c-index calculation the remaining members were used unchanged from the original T5 Algorithm. The range in square brackets lists the estimated range of the coefficients: mean+/−3 standard deviations.

Member 1 of T5:
Original member 1:

+0.41 [0.21 ... 0.61]*BIRC5 −0.33 [−0.57 ...
−0.09]*RBBP8 c-indices: trainSet=0.724, independentCohort=0.705 replace BIRC5 by TOP2A in member 1:

+0.47 [0.24 ... 0.69]*TOP2A −0.34 [−0.58 ...
−0.10]*RBBP8 c-indices: trainSet=0.734, independentCohort=0.694 replace BIRC5 by RACGAP1 in member 1:

+0.69 [0.37 ... 1.00]*RACGAP1 −0.33 [−0.57 ...
−0.09]*RBBP8 c-indices: trainSet=0.736, independentCohort=0.743 replace RBBP8 by CELSR2 in member 1:

+0.38 [0.19 ... 0.57]*BIRC5 −0.18 [−0.41 ...
0.05]*CELSR2 c-indices: trainSet=0.726, independentCohort=0.680 replace RBBP8 by PGR in member 1:

+0.35 [0.15 ... 0.54]*BIRC5 −0.09 [−0.23 ...
0.05]*PGR c-indices: trainSet=0.727, independentCohort=0.731

Member 2 of T5:
Original member 2:

+0.38 [0.15 ... 0.61]*UBE2C −0.30 [−0.55 ...
−0.06]*IL6ST c-indices: trainSet=0.724, independentCohort=0.725 replace UBE2C by RACGAP1 in member 2:

+0.65 [0.33 ... 0.96]*RACGAP1 −0.38 [−0.62 ...
−0.13]*IL6ST c-indices: trainSet=0.735, independentCohort=0.718 replace UBE2C by TOP2A in member 2:

+0.42 [0.20 ... 0.65]*TOP2A −0.38 [−0.62 ...
−0.13]*IL6ST c-indices: trainSet=0.734, independentCohort=0.700 replace IL6ST by INPP4B in member 2:

+0.40 [0.17 ... 0.62]*UBE2C −0.25 [−0.55 ...
0.05]*INPP4B c-indices: trainSet=0.725, independentCohort=0.686 replace IL6ST by MAPT in member 2:

+0.45 [0.22 ... 0.69]*UBE2C −0.14 [−0.28 ...
0.01]*MAPT c-indices: trainSet=0.727, independentCohort=0.711

Member 3 of T5:
Original member 3:

−0.28 [−0.43 ... −0.12]*AZGP1+0.42 [0.16 ...
0.68]*DHCR7 c-indices: trainSet=0.724, independentCohort=0.705 replace AZGP1 by PIP in member 3:

−0.10 [−0.18 ... −0.02]*PIP+0.43 [0.16 ... 0.70]
*DHCR7 c-indices: trainSet=0.725, independentCohort=0.692 replace AZGP1 by EPHX2 in member 3:

−0.23 [−0.43 . . . −0.02]*EPHX2+0.37 [0.10 . . . 0.64]*DHCR7 c-indices: trainSet=0.719, independentCohort=0.698 replace AZGP1 by PLAT in member 3:

−0.23 [−0.40 . . . −0.06]*PLAT+0.43 [0.18 . . . 0.68]*DHCR7 c-indices: trainSet=0.712, independentCohort=0.715 replace DHCR7 by AURKA in member 3:

−0.23 [−0.39 . . . −0.06]*AZGP1+0.34 [0.10 . . . 0.58]*AURKA c-indices: trainSet=0.716, independentCohort=0.733

Member 4 of T5:
Original member 4:

−0.18 [−0.31 . . . −0.06]*MGP −0.13 [−0.25 . . . −0.02]*STC2 c-indices: trainSet=0.724, independentCohort=0.705 replace MGP by APOD in member 4:

−0.16 [−0.30 . . . −0.03]*APOD −0.14 [−0.26 . . . −0.03]*STC2 c-indices: trainSet=0.717, independentCohort=0.679 replace MGP by EGFR in member 4:

−0.21 [−0.37 . . . −0.05]*EGFR −0.14 [−0.26 . . . −0.03]*STC2 c-indices: trainSet=0.715, independentCohort=0.708 replace STC2 by INPP4B in member 4:

−0.18 [−0.30 . . . −0.05]*MGP −0.22 [−0.53 . . . 0.08]*INPP4B c-indices: trainSet=0.719, independentCohort=0.693 replace STC2 by SEC14L2 in member 4:

−0.18 [−0.31 . . . −0.06]*MGP −0.27 [−0.49 . . . −0.06]*SEC14L2 c-indices: trainSet=0.718, independentCohort=0.681

One can see that replacements of single genes experimentally identified for a quantification with kinetic PCR normally affect the predictive performance of the T5 algorithm, assessed by the c-index only insignificantly.

The following table (Tab. 8) shows potential replacement gene candidates for the genes of T5 algorithm. Each gene candidate is shown in one table cell: The gene name is followed by the bracketed absolute Pearson correlation coefficient of the expression of the original gene in the T5 Algorithm and the replacement candidate, and the HG-U133A probe set ID.

TABLE 8

| BIRC5 | RBBP8 | UBE2C | IL6ST | AZGP1 | DHCR7 | MGP | STC2 |
|---|---|---|---|---|---|---|---|
| UBE2C (0.775), 202954_at | CELSR2 (0.548), 204029_at | BIRC5 (0.775), 202095_s_at | INPP4B (0.477), 205376_at | PIP (0.530), 206509_at | AURKA (0.345), 204092_s_at | APOD (0.368), 201525_at | INPP4B (0.500), 205376_at |
| TOP2A (0.757), 201292_at | PGR (0.392), 208305_at | RACGAP1 (0.756), 222077_s_at | STC2 (0.450), 203438_at | EPHX2 (0.369), 209368_at | BIRC5 (0.323), 202095_s_at | IL6ST (0.327), 212196_at | IL6ST (0.450), 212196_at |
| RACGAP1 (0.704), 222077_s_at | STC2 (0.361), 203438_at | TOP2A (0.753), 201292_at | MAPT (0.440), 206401_s_at | PLAT (0.366), 201860_s_at | UBE2C (0.315), 202954_at | EGFR (0.308), 201983_s_at | SEC14L2 (0.417), 204541_at |
| AURKA (0.681), 204092_s_at | ABAT (0.317), 209459_s_at | AURKA (0.694), 204092_s_at | SCUBE2 (0.418), 219197_s_at | SEC14L2 (0.351), 204541_at | | | MAPT (0.414), 206401_s_at |
| NEK2 (0.680), 204026_s_at | IL6ST (0.311), 212196_at | NEK2 (0.684), 204026_s_at | ABAT (0.389), 209459_s_at | SCUBE2 (0.331), 219197_s_at | | | CHPT1 (0.410), 221675_s_at |
| E2F8 (0.640), 219990_at | | E2F8 (0.652), 219990_at | PGR (0.377), 208305_at | PGR (0.302), 208305_at | | | ABAT (0.409), 209459_s_at |
| PCNA (0.544), 201202_at | | PCNA (0.589), 201202_at | SEC14L2 (0.356), 204541_at | | | | SCUBE2 (0.406), 219197_s_at |
| CYBRD1 (0.462), 217889_s_at | | CYBRD1 (0.486), 217889_s_at | ESR1 (0.353), 205225_at | | | | ESR1 (0.394), 205225_at |
| DCN (0.439), 209335_at | | ADRA2A (0.391), 209869_at | GJA1 (0.335), 201667_at | | | | RBBP8 (0.361), 203344_s_at |
| ADRA2A (0.416), 209869_at | | DCN (0.384), 209335_at | MGP (0.327), 202291_s_at | | | | PGR (0.347), 208305_at |
| SQLE (0.415), 209218_at | | SQLE (0.369), 209218_at | EPHX2 (0.313), 209368_at | | | | PTPRT (0.343), 205948_at |
| CXCL12 (0.388), 209687_at | | CCND1 (0.347), 208712_at | RBBP8 (0.311), 203344_s_at | | | | HSPA2 (0.317), 211538_s_at |
| EPHX2 (0.362), 209368_at | | ASPH (0.344), 210896_s_at | PTPRT (0.303), 205948_at | | | | PTGER3 (0.314), 210832_x_at |
| ASPH (0.352), 210896_s_at | | CXCL12 (0.342), 209687_at | PLAT (0.301), 201860_s_at | | | | |
| PRSS16 (0.352), 208165_s_at | | PIP (0.328), 206509_at | | | | | |
| EGFR (0.346), 201983_s_at | | PRSS16 (0.326), 208165_s_at | | | | | |
| CCND1 (0.331), 208712_at | | EGFR (0.320), 201983_s_at | | | | | |
| TRIM29 (0.325), 202504_at | | DHCR7 (0.315), 201791_s_at | | | | | |
| DHCR7 (0.323), | | EPHX2 (0.315), | | | | | |

TABLE 8-continued

| BIRC5 | RBBP8 | UBE2C | IL6ST | AZGP1 | DHCR7 | MGP | STC2 |
|---|---|---|---|---|---|---|---|
| 201791_s_at PIP (0.308), 206509_at TFAP2B (0.306), 214451_at WNT5A (0.303), 205990_s_at APOD (0.301), 201525_at PTPRT (0.301), 205948_at | | 209368_at TRIM29 (0.311), 202504_at | | | | | |

The following table (Tab. 9) lists qRT-PCR primer and probe sequences used for the table above.

TABLE 9

| gene | probe | forward primer | reverse primer |
|---|---|---|---|
| ABAT | TCGCCCTAAGAGGCTCTTCCTC | GGCAACTTGAGGTCTGACTTTTG | GGTCAGCTCACAAGTGGTGTGA |
| ADRA2A | TTGTCCTTTCCCCCCTCCGTGC | CCCCAAGAGCTGTTAGGTATCAA | TCAATGACATGATCTCAACCAGAA |
| APOD | CATCAGCTCTCAACTCCTGGTTTAACA | ACTCACTAATGGAAAACGGAAAGATC | TCACCTTCGATTTGATTCACAGTT |
| ASPH | TGGGAGGAAGGCAAGGTGCTCATC | TGTGCCAACGAGACCAAGAC | TCGTGCTCAAAGGAGTCATCA |
| AURKA | CCGTCAGCCTGTGCTAGGCAT | AATCTGGAGGCAAGGTTCGA | TCTGGATTTGCCTCCTGTGAA |
| BIRC5 | AGCCAGATGACGACCCCATAGAGGAACA | CCCAGTGTTTCTTCTGCTTCAAG | CAACCGGACGAATGCTTTTT |
| CCND1 | | | |
| CELSR2 | ACTGACTTTCCTTCTGGAGCAGGTGGC | TCCAAGCATGTATTCCAGACTTGT | TGCCCACAGCCTCTTTTTCT |
| CHPT1 | CCACGGCCACCGAAGAGGCAC | CGCTCGTGCTCATCTCCTACT | CCCAGTGCACATAAAAGGTATGTC |
| CXCL12 | CCACAGCAGGGTTTCAGGTTCC | GCCACTACCCCCTCCTGAA | TCACCTTGCCAACAGTTCTGAT |
| CYBRD1 | AGGGCATCGCCATCATCGTC | GTCACCGGCTTCGTCTTCA | CAGGTCCACGGCAGTCTGT |
| DCN | TCTTTTCAGCAACCCGGTCCA | AAGGCTTCTTATTCGGGTGTGA | TGGATGGCTGTATCTCCCAGTA |
| DHCR7 | TGAGCGCCCACCCTCTCGA | GGGCTCTGCTTCCCGATT | AGTCATAGGGCAAGCAGAAAATTC |
| E2F8 | CAGGATACCTAATCCCTCTCACGCAG | AAATGTCTCCGCAACCTTGTTC | CTGCCCCCAGGGATGAG |
| EGFR | | | |
| EPHX2 | TGAAGCGGGAGGACTTTTTGTAAA | CGATGAGAGTGTTTTATCCATGCA | GCTGAGGCTGGGCTCTTCT |
| ESR1 | ATGCCCTTTTGCCGATGCA | GCCAAATTGTGTTTGATGGATTAA | GACAAAACCGAGTCACATCAGTAATAG |
| GJA1 | TGCACAGCCTTTTGATTTCCCCGAT | CGGGAAGCACCATCTCTAACTC | TTCATGTCCAGCAGCTAGTTTTTT |
| HSPA2 | CAAGTCAGCAAACACGCAAAA | CATGCACGAACTAATCAAAAATGC | ACATTATTCGAGGTTTCTCTTTAATGC |
| IL6ST | CAAGCTCCACCTTCCAAAGGACCT | CCCTGAATCCATAAAGGCATACC | CAGCTTCGTTTTTCCCTACTTTTT |
| INPP4B | TCCGAGCGCTGGATTGCATGAG | GCACCAGTTACACAAGGACTTCTTT | TCTCTATGCGGCATCCTTCTC |
| MAPT | AGACTATTTGCACACTGCCGCCT | GTGGCTCAAAGGATAATATCAAACAC | ACCTTGCTCAGGTCAACTGGTT |
| MGP | CCTTCATATCCCCTCAGCAGAGATGG | CCTTCATTAACAGGAGAAATGCAA | ATTGAGCTCGTGGACAGGCTTA |
| NEK2 | TCCTGAACAAATGAATCGCATGTCCTACAA | ATTTGTTGGCACACCTTATTACATGT | AAGCAGCCCAATGACCAGATa |
| PCNA | AAATACTAAAATGCGCCGGCAATGA | GGGCGTGAACCTCACCAGTA | CTTCGGCCCTTAGTGTAATGATATC |
| PGR | TTGATAGAAACGCTGTGAGCTCGA | AGCTCATCAAGGCAATTGGTTT | ACAAGATCATGCAAGTTATCAAGAAGTT |
| PIP | TGCATGGTGGTTAAAACTTACCTCA | TGCTTGCAGTTCAAACAGAATTG | CACCTTGTAGAGGGATGCTGCTA |
| PLAT | CAGAAAGTGGCCATGCCACCCTG | TGGGAAGACATGAATGCACACTA | GGAGGTTGGGCTTTAGCTGAA |

TABLE 9-continued

| gene | probe | forward primer | reverse primer |
|---|---|---|---|
| PRSS16 | CACTGCCGGTCACCCACACCA | CTGAGGAGCACAGAACCTCAACT | CGAACTCGGTACATGTCTGATACAA |
| PTGER3 | TCGGTCTGCTGGTCTCCGCTCC | CTGATTGAAGATCATTTTCAACATCA | GACGGCCATTCAGCTTATGG |
| PTPRT | TTGGCTTCTGGACACCCTCACA | GAGTTGTGGCCTCTACCATTGC | GAGCGGGAACCTTGGGATAG |
| RACGAP1 | ACTGAGAATCTCCACCCGGCGCA | TCGCCAACTGGATAAATTGGA | GAATGTGCGGAATCTGTTTGAG |
| RBBP8 | ACCGATTCCGCTACATTCCACCCAAC | AGAAATTGGCTTCCTGCTCAAG | AAAACCAACTTCCCAAAAATTCTCT |
| SCUBE2 | CTAGAGGGTTCCAGGTCCCATACGTGACATA | TGTGGATTCAGTTCAAGTCCAATG | CCATCTCGAACTATGTCTTCAATGAGT |
| SEC14L2 | TGGGAGGCATGCAACGCGTG | AGGTCTTACTAAGCAGTCCCATCTCT | CGACCGGCACCTGAACTC |
| SQLE | TATGCGTCTCCCAAAAGAAGAACACCTCG | GCAAGCTTCCTTCCTCCTTCA | CCTTTAGCAGTTTTCTCCATAGTTTTATATC |
| STC2 | TCTCACCTTGACCCTCAGCCAAG | ACATTTGACAAATTTCCCTTAGGATT | CCAGGACGCAGCTTTACCAA |
| TFAP2B | CAACACCACCACTAACAGGCACACGTC | GGCATGGACAAGATGTTCTTGA | CCTCCTTGTCGCCAGTTTTACT |
| TOP2A | CAGATCAGGACCAAGATGGTTCCCACAT | CATTGAAGACGCTTCGTTATGG | CCAGTTGTGATGGATAAAATTAATCAG |
| TRIM29 | TGCTGTCTCACTACCGGCCATTCTACG | TGGAAATCTGGCAAGCAGACT | CAATCCCGTTGCCTTTGTTG |
| UBE2C | TGAACACACATGCTGCCGAGCTCTG | CTTCTAGGAGAACCCAACATTGATAGT | GTTTCTTGCAGGTACTTCTTAAAAGCT |
| WNT5A | TATTCACATCCCCTCAGTTGCAGTGAATTG | CTGTGGCTCTTAATTTATTGCATAATG | TTAGTGCTTTTTGCTTTCAAGATCTT |

A second alternative for unsupervised selection of possible gene replacement candidates is based on Affymetrix data only. This has the advantage that it can be done solely based on already published data (e.g. from www.ncbi.nlm.nih.gov/geo/). The following table (Tab. 10) lists HG-U133a probe set replacement candidates for the probe sets used in algorithms T1-T5. This is based on training data of these algorithms. The column header contains the gene name and the probe set ID in bold. Then, the 10 best-correlated probe sets are listed, where each table cell contains the probe set ID, the correlation coefficient in brackets and the gene name.

TABLE 10

| UBE2C 202954_at | BIRC5 202095_s_at | DHCR7 201791_s_at | RACGAP1 222077_s_at | AURKA 204092_s_at | PVALB 205336_at | NMU 206023_at | STC2 203438_at |
|---|---|---|---|---|---|---|---|
| 210052_s_at (0.82) TPX2 | 202954_at (0.82) UBE2C | 201790_s_at (0.66) DHCR7 | 218039_at (0.79) NUSAP1 | 208079_s_at (-0.33) STK6 | 208683_at (-0.33) CAPN2 | 205347_s_at (0.45) TMSL8 | 203439_s_at (0.88) STC2 |
| 202095_s_at (0.82) BIRC5 | 218039_at (0.81) NUSAP1 | 202218_at (0.48) FADS2 | 214710_s_at (0.78) CCNB1 | 202954_at (0.80) UBE2C | 219682_s_at (0.30) TBX3 | 203764_at (0.45) DLG7 | 212496_s_at (0.52) JMJD2B |
| 218009_s_at (0.82) PRC1 | 218009_s_at (0.79) PRC1 | 202580_x_at (0.47) FOXM1 | 203764_at (0.77) DLG7 | 210052_s_at (0.77) TPX2 | 218704_at (0.30) FLJ20315 | 203554_x_at (0.44) PTTG1 | 219440_at (0.52) RAI2 |
| 203554_x_at (0.82) PTTG1 | 202705_at (0.78) CCNB2 | 208944_at (-0.46) TGFBR2 | 204026_s_at (0.77) ZWINT | 202095_s_at (0.77) BIRC5 |  | 204962_s_at (0.44) CENPA | 215867_x_at (0.51) CA12 |
| 208079_s_at (0.81) STK6 | 204962_s_at (0.78) CENPA | 202954_at (0.46) UBE2C | 218009_s_at (0.76) PRC1 | 203554_x_at (0.76) PTTG1 |  | 204825_at (0.43) MELK | 214164_x_at (0.50) CA12 |
| 202705_at (0.81) CCNB2 | 203554_x_at (0.78) PTTG1 | 209541_at (-0.45) IGF1 | 204641_at (0.76) NEK2 | 218009_s_at (0.75) PRC1 |  | 209714_s_at (0.41) CDKN3 | 204541_at (0.50) SEC14L2 |
| 218039_at (0.81) NUSAP1 | 208079_s_at (0.78) STK6 | 201059_at (0.45) CTTN | 204444_at (0.75) KIF11 | 201292_at (0.73) TOP2A |  | 219918_s_at (0.41) ASPM | 203963_at (0.50) CA12 |
| 202870_s_at (0.80) CDC20 | 210052_s_at (0.77) TPX2 | 200795_at (-0.45) SPARCL1 | 202705_at (0.75) CCNB2 | 214710_s_at (0.73) CCNB1 |  | 207828_s_at (0.41) CENPF | 212495_at (0.50) JMJD2B |
| 204092_s_at (0.80) STK6 | 202580_x_at (0.77) FOXM1 | 218009_s_at (0.45) PRC1 | 203362_s_at (0.75) MAD2L1 | 204962_s_at (0.73) CENPA |  | 202705_at (0.41) CCNB2 | 208614_s_at (0.49) FLNB |
| 209408_at (0.80) KIF2C | 204092_s_at (0.77) STK6 | 218542_at (0.45) C10orf3 | 202954_at (0.75) UBE2C | 218039_at (0.73) NUSAP1 |  | 219787_s_at (0.40) ECT2 | 213933_at (0.49) PTGER3 |

| AZGP1 209309_at | RBBP8 203344_s_at | IL6ST 212196_at | MGP 202291_s_at | PTGER3 213933_at | CXCL12 209687_at | ABAT 209460_at | CDH1 201131_s_at |
|---|---|---|---|---|---|---|---|
| 217014_s_at (0.92) AZGP1 | 36499_at (0.49) CELSR2 | 212195_at (0.85) IL6ST | 201288_at (0.46) ARHGDIB | 210375_at (0.74) PTGER3 | 204955_at (0.81) SRPX | 209459_s_at (0.92) ABAT | 201130_s_at (0.57) CDH1 |
| 206509_at (0.52) PIP | 204029_at (0.45) CELSR2 | 204864_s_at (0.75) IL6ST | 219768_at (0.42) VTCN1 | 210831_s_at (0.74) PTGER3 | 209335_at (0.81) DCN | 206527_at (0.63) ABAT | 221597_s_at (0.40) HSPC171 |
| 204541_at (0.46) SEC14L2 | 208305_at (0.45) PGR | 211000_s_at (0.68) IL6ST | 202849_x_at (-0.41) GRK6 | 210374_x_at (0.73) PTGER3 | 211896_s_at (0.81) DCN | 213392_at (0.54) MGC35048 | 203350_at (0.38) AP1G1 |
| 200670_at (0.45) XBP1 | 205380_at (0.43) PDZK1 | 214077_x_at (0.61) MEIS4 | 205382_s_at (0.40) DF | 210832_x_at (0.73) PTGER3 | 201893_x_at (0.81) DCN | 221666_s_at (0.49) PYCARD | 209163_at (0.36) CYB561 |

TABLE 10-continued

| | | | | | | | |
|---|---|---|---|---|---|---|---|
| 209368_at (0.45) EPHX2 | 203303_at (0.41) TCTE1L | 204863_s_at (0.58) IL6ST | 200099_s_at (0.39) RPS3A | 210834_s_at (0.55) PTGER3 | 203666_at (0.80) CXCL12 | 218016_s_at (0.48) POLR3E | 210239_at (0.35) IRX5 |
| 218627_at (−0.43) FLJ11259 | 205280_at (0.38) GLRB | 202089_s_at (0.57) SLC39A6 | 221591_s_at (−0.37) FAM64A | 210833_at (0.55) PTGER3 | 211813_x_at (0.80) DCN | 214440_at (0.46) NAT1 | 200942_s_at (0.34) HSBP1 |
| 202286_s_at (0.43) TACSTD2 | 205279_s_at (0.38) GLRB | 210735_s_at (0.56) CA12 | 214629_x_at (0.37) RTN4 | 203438_at (0.49) STC2 | 208747_s_at (0.79) C1S | 204981_at (0.45) SLC22A18 | 209157_at (0.34) DNAJA2 |
| 213832_at (0.42)— | 203685_at (0.38) BCL2 | 200648_s_at (0.52) GLUL | 200748_s_at (0.37) FTH1 | 203439_s_at (0.46) STC2 | 203131_at (0.78) PDGFRA | 212195_at (0.45) IL6ST | 210715_s_at (0.33) SPINT2 |
| 204288_s_at (0.41) SORBS2 | 203304_at (−0.38) BAMBI | 214552_s_at (0.52) RABEP1 | 209408_at (−0.37) KIF2C | 212195_at (0.41) IL6ST | 202994_s_at (0.78) FBLN1 | 204497_at (0.45) ADCY9 | 203219_s_at (0.33) APRT |
| 202376_at (0.41) SERPINA3 | 205862_at (0.36) GREB1 | 219197_s_at (0.51) SCUBE2 | 218726_at (−0.36) DKFZp762E1312 | 217764_s_at (0.40) RAB31 | 208944_at (0.78) TGFBR2 | 215867_x_at (0.45) CA12 | 218074_at (0.33) FAM96B |

Figure 3:
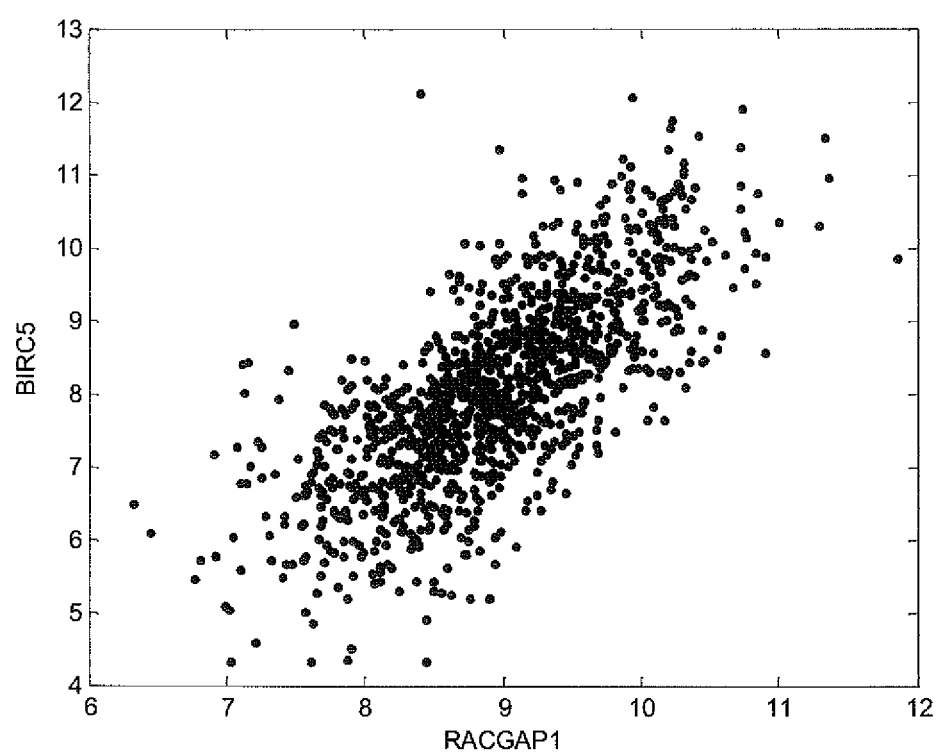
FIG. 3 shows joint distribution scatter plot of expressions in training data.

After selection of a gene or a probe set one has to define a mathematical mapping between the expression values of the gene to replace and those of the new gene. There are several alternatives which are discussed here based on the example "replace delta-Ct values of BIRC5 by RACGAP1". In the training data the joint distribution of expressions looks like in FIG. 3.

The Pearson correlation coefficient is 0.73.

One approach is to create a mapping function from RACGAP1 to BIRC5 by regression. Linear regression is the first choice and yields in this example

BIRC5=1.22*RACGAP1 −2.85.

Using this equation one can easily replace the BIRC5 variable in e.g. algorithm T5 by the right hand side. In other examples robust regression, polynomial regression or univariate nonlinear pre-transformations may be adequate.

The regression method assumes measurement noise on BIRC5, but no noise on RACGAP1. Therefore the mapping is not symmetric with respect to exchangeability of the two variables. A symmetric mapping approach would be based on two univariate z-transformations.

z=(BIRC5−mean(BIRC5))/std(BIRC5) and
z=(RACGAP1−mean(RACGAP1))/std(RACGAP1)
z=(BIRC5 −8.09)/1.29=(RACGAP1 −8.95)/0.77
BIRC5=1.67*RACGAP1 +−6.89

Again, in other examples, other transformations may be adequate:

normalization by median and/or mad, nonlinear mappings, or others.

The invention claimed is:

1. A method for treating a patient having an estrogen receptor positive and HER2 negative breast tumor, the method comprising:
   determining whether the patient will benefit from cytotoxic chemotherapy by:
   (1) determining in a sample from the tumor the RNA expression level values of a set of marker genes, the set of marker genes comprising at least 3 of the following genes: UBE2C, BIRC5, DHCR7, STC2, AZGP1, RBBP8, IL6ST, and MGP;
   (2) combining the expression level values determined in step (1) to yield a test combined score; and
   administering a treatment regimen comprising a cytotoxic chemotherapy to the patient if the test combined score exceeds a reference combined score, or
   administering a treatment regimen comprising a non-cytotoxic therapy to the patient if the test combined score does not exceed the reference combined score.

2. The method of claim 1 comprising detecting in a sample from the tumor the RNA expression level values of a set of marker genes comprising the following genes: UBE2C, BIRC5, DHCR7, STC2, AZGP1, RBBP8, IL6ST, and MGP.

3. The method of claim 1, wherein the patient has received endocrine therapy or endocrine treatment has been prescribed for the patient.

4. The method of claim 3, wherein the endocrine therapy comprises tamoxifen or an aromatase inhibitor.

5. The method of claim 1, wherein the expression level value is detected as a Messenger-RNA expression level value.

6. The method of claim 5, wherein the expression level value is detected by at least one of
   (a) a PCR-based method,
   (b) a microarray-based method, or
   (c) a hybridization-based method.

7. The method of claim 1, wherein the sample is a formalin-fixed paraffin-embedded sample.

8. The method of claim 1, wherein the expression level value of at least one marker gene is determined as a pattern of expression relative to at least one reference gene or to a computed average expression value.

9. The method of claim 1, wherein step (1) comprises applying an algorithm to values representative of expression levels of given genes.

10. The method of claim 9, wherein the algorithm is a linear combination of the values representative of expression levels of given genes.

11. The method of claim 10, wherein at least one of the values representative of expression levels of given genes is multiplied with a coefficient.

12. The method of claim 1, wherein step (1) comprises processing information regarding nodal status of the patient.

13. The method of claim 12, wherein the information regarding nodal status is a first numerical value if the nodal status is negative, the information is a second numerical value if the nodal status is positive, and the information is either the first numerical value, the second numerical value, or a third numerical value if the nodal status is unknown.

14. The method of claim 1, wherein the non-cytotoxic therapy is an endocrine therapy.

15. The method of claim 14, wherein administering the endocrine therapy comprises administration of tamoxifen or derivative thereof.

16. The method of claim 1, wherein the set of marker genes comprises at least 4 of the following genes: UBE2C, BIRC5, DHCR7, STC2, AZGP1, RBBP8, IL6ST, and MGP.

17. The method of claim 1, wherein the set of marker genes comprises at least 5 of the following genes: UBE2C, BIRC5, DHCR7, STC2, AZGP1, RBBP8, IL6ST, and MGP.

18. The method of claim 1, wherein the set of marker genes comprises at least 6 of the following genes: UBE2C, BIRC5, DHCR7, STC2, AZGP1, RBBP8, IL6ST, and MGP.

19. The method of claim 1, wherein the set of marker genes comprises at least 7 of the following genes: UBE2C, BIRC5, DHCR7, STC2, AZGP1, RBBP8, IL6ST, and MGP.

* * * * *